US008043338B2

(12) United States Patent
Dant

(10) Patent No.: US 8,043,338 B2
(45) Date of Patent: Oct. 25, 2011

(54) ADJUSTABLE ASSEMBLY FOR CORRECTING SPINAL ABNORMALITIES

(75) Inventor: Jack A. Dant, St. Paul, MN (US)

(73) Assignee: Zimmer Spine, Inc., Minneapolis, MN (US)

(*) Notice: Subject to any disclaimer, the term of this patent is extended or adjusted under 35 U.S.C. 154(b) by 342 days.

(21) Appl. No.: 12/327,688

(22) Filed: Dec. 3, 2008

(65) Prior Publication Data

US 2010/0137911 A1 Jun. 3, 2010

(51) Int. Cl.
*A61B 17/70* (2006.01)
(52) U.S. Cl. ..... 606/252; 606/250; 606/251; 623/18.11; 623/18.12
(58) Field of Classification Search .......... 606/246, 606/250–253, 260, 279, 57, 58, 90, 105, 606/282; 623/18.12, 17.11, 18.11, 3.11; 600/9, 12
See application file for complete search history.

(56) References Cited

U.S. PATENT DOCUMENTS

| | | | |
|---|---|---|---|
| 5,084,049 A * | 1/1992 | Asher et al. ............. | 606/251 |
| 5,413,602 A | 5/1995 | Metz-Stavenhagen | |
| 5,928,232 A | 7/1999 | Howland et al. | |
| 6,296,643 B1 | 10/2001 | Hopf et al. | |
| 6,299,613 B1 | 10/2001 | Ogilvie et al. | |
| 6,416,515 B1 | 7/2002 | Wagner | |
| 6,458,131 B1 | 10/2002 | Ray | |
| 6,551,320 B2 | 4/2003 | Lieberman | |
| 6,613,050 B1 | 9/2003 | Wagner et al. | |
| 6,623,484 B2 | 9/2003 | Betz et al. | |
| 6,669,729 B2 | 12/2003 | Chin | |
| 6,783,528 B2 | 8/2004 | Vincent-Prestigiacomo | |
| 6,802,844 B2 | 10/2004 | Ferree | |
| 6,835,207 B2 | 12/2004 | Zacouto et al. | |
| 7,029,472 B1 | 4/2006 | Fortin | |
| 7,131,972 B2 | 11/2006 | Mazda et al. | |
| 7,207,991 B2 | 4/2007 | Michelson | |
| 7,282,064 B2 | 10/2007 | Chin | |
| 7,335,201 B2 | 2/2008 | Doubler et al. | |
| 2004/0030395 A1 | 2/2004 | Blunn et al. | |
| 2004/0106921 A1 | 6/2004 | Cheung et al. | |
| 2006/0009768 A1 | 1/2006 | Ritland | |
| 2006/0047282 A1 | 3/2006 | Gordon | |

(Continued)

OTHER PUBLICATIONS

Werch Takes, Joanna, "Invisible Joints . . . Magic, or Lamello?", on the world wide web at Woodworking.com—eZine Tool Preview, 2 pgs, From Mar. 11-Mar. 24, 2003 issue of Woodworker's Journal eZine.

(Continued)

*Primary Examiner* — Eduardo C Robert
*Assistant Examiner* — Christina Negrelli
(74) *Attorney, Agent, or Firm* — Seager Tufte Wickhem LLC

(57) ABSTRACT

An assembly for post-operatively treating an abnormal curvature of vertebrae of a spinal column. The assembly includes an elongate member extending in a generally vertical direction along a posterior side of the spinal column and a transverse member fastened to a vertebra of the spinal column with a plurality of fasteners and extending in a generally horizontal direction. The transverse member has a threaded region. The assembly further includes a coupler coupling the elongate member to the transverse member. The coupler includes a rotating member threadedly engaged with the threaded region of the transverse member. Rotation of the rotating member provides lateral movement of the transverse member relative to the elongate member, thereby moving the vertebra in a horizontal direction and applying a corrective force to the vertebra.

38 Claims, 13 Drawing Sheets

U.S. PATENT DOCUMENTS

| | | | |
|---|---|---|---|
| 2006/0052786 A1 | 3/2006 | Dant et al. | |
| 2006/0058792 A1 | 3/2006 | Hynes | |
| 2006/0089643 A1 | 4/2006 | Mujwid | |
| 2006/0155279 A1 | 7/2006 | Ogilvie | |
| 2006/0195090 A1 | 8/2006 | Suddaby | |
| 2007/0233098 A1 | 10/2007 | Mastrorio et al. | |
| 2007/0270803 A1* | 11/2007 | Giger et al. | 606/60 |
| 2008/0021465 A1 | 1/2008 | Shadduck et al. | |
| 2008/0033436 A1 | 2/2008 | Song et al. | |
| 2008/0140133 A1 | 6/2008 | Allard et al. | |
| 2008/0140202 A1 | 6/2008 | Allard et al. | |
| 2008/0269805 A1 | 10/2008 | Dekutoski et al. | |
| 2009/0012565 A1 | 1/2009 | Sachs et al. | |
| 2009/0204154 A1 | 8/2009 | Kiester | |

OTHER PUBLICATIONS

Product Information Brochure, "Step by Step", 2 pgs., no date indicated.

Product Information Brochure, "Thus Invis Functions," 1 pg., no date indicated.

Product Information Brochure, "INVIS®, Invisible, detachable joining." Invis (North America), Inc., Irvine, CA, 2 pgs, 2003.

* cited by examiner

ADJUSTABLE ASSEMBLY FOR CORRECTING SPINAL ABNORMALITIES

TECHNICAL FIELD

The disclosure is directed to a system, assembly, apparatus and method of correcting spinal abnormalities. More particularly, the disclosure is directed to a system, assembly, apparatus and method of post-operatively correcting abnormal curvature of the spinal column.

BACKGROUND

The spinal column of a patient includes a plurality of vertebrae linked to one another by facet joints and an intervertebral disc located between adjacent vertebrae. In a healthy spinal column, viewed posteriorly, the vertebrae are aligned along the sagittal plane of the patient. Viewed laterally, the spinal column exhibits several curves corresponding to different regions of the spinal column, named the cervical, thoracic, and lumbar curves.

There are many types of spinal column disorders and abnormal curvatures of the spinal column including scoliosis (abnormal lateral curvature of the spine), kyphosis (abnormal forward curvature of the spine, usually in the thoracic spine), excess lordosis (abnormal backward curvature of the spine, usually in the lumbar spine), spondylolisthesis (forward displacement of one vertebra over another, usually in the lumbar or cervical spine), as well as other disorders caused by abnormalities, disease or trauma.

Various correction systems have been proposed and used in attempting to correct abnormal curvatures of the spinal column. However, each of these correction systems includes deficiencies making the correction system less than optimal. For instance, many systems require some form of repeated surgeries to achieve a satisfactory correction of the curvature, exert excessive stresses on anatomical structures of the spinal column and/or include limitations as to the extent of correction which is possible.

Accordingly, there is an ongoing need to provide alternative apparatus, devices, assemblies, systems and/or methods that can function to correct spinal abnormalities, such as abnormal curvature of the spinal column.

SUMMARY

The disclosure is directed to several alternative designs, materials and methods of manufacturing medical device structures and assemblies.

Accordingly, one illustrative embodiment is an assembly for post-operatively treating an abnormal curvature of vertebrae of a spinal column. The assembly includes an elongate member extending in a generally vertical direction along a posterior side of the spinal column and a transverse member fastened to a vertebra of the spinal column with a plurality of fasteners and extending in a generally horizontal direction. The transverse member has a threaded region. The assembly further includes a coupler coupling the elongate member to the transverse member. The coupler includes a rotating member threadedly engaged with the threaded region of the transverse member. Rotation of the rotating member provides lateral movement of the transverse member relative to the elongate member, thereby moving the vertebra in a horizontal direction.

Another illustrative embodiment is an assembly for post-operatively treating an abnormal curvature of vertebrae of a spinal column. The assembly includes an elongate member extending in a generally vertical direction along a posterior side of at least three vertebrae of the spinal column. A first transverse member is fixedly attached to a first vertebra of the spinal column with a plurality of fasteners. The first transverse member includes a portion extending generally perpendicular to the elongate member. A second transverse member is fixedly attached to a second vertebra of the spinal column with a plurality of fasteners. The second transverse member includes a portion extending generally perpendicular to the elongate member. A third transverse member is fixedly attached to a third vertebra of the spinal column with a plurality of fasteners. The third transverse member includes a portion extending generally perpendicular to the elongate member. A first coupler couples the elongate member to the first transverse member. The first coupler includes a fine adjustment mechanism providing post-operative movement of the first transverse member in a horizontal direction relative to the elongate member. A second coupler couples the elongate member to the second transverse member. The second coupler includes a fine adjustment mechanism providing post-operative movement of the second transverse member in a horizontal direction relative to the elongate member. A third coupler couples the elongate member to the third transverse member. The third coupler includes a fine adjustment mechanism providing post-operative movement of the third transverse member in a horizontal direction relative to the elongate member.

Yet another illustrative embodiment is a method of treating an abnormal curvature of vertebrae of a spinal column of a patient. The method includes performing the following steps during a surgical operation:

placing an elongate member along a posterior side of the spinal column in a generally vertical direction;

connecting a transverse member to a first vertebra with a plurality of fasteners, the transverse member including a threaded region; and coupling the transverse member to the elongate member with a coupler, the coupler including a rotating member having a threaded portion engaging the threaded region of the transverse member.

The method further includes performing the following steps post-operatively:

rotating the rotating member, thereby moving the transverse member in a horizontal direction relative to the elongate member, wherein rotation of the rotating member exerts a corrective force to the first vertebra.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which.

Figure 1A:
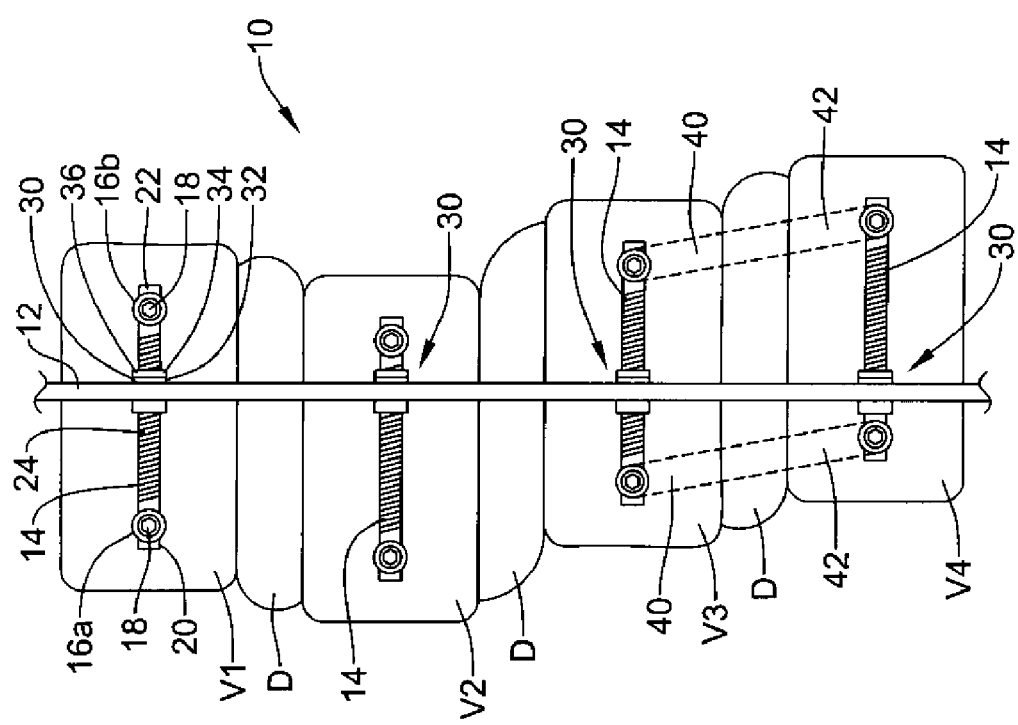
FIG. 1A shows an illustrative embodiment of an assembly for correcting an abnormal curvature of a spinal column.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

As used in this specification and the appended claims, the term "vertical" is used in its conventional manner as extending in a superior-inferior direction parallel to the sagittal plane of a patient. Thus, the term "vertical" is intended to refer to a direction generally parallel to the longitudinal axis of a spinal column of a patient.

As used in this specification and the appended claims, the term "horizontal" is used in its conventional manner as extending perpendicular to vertical. Thus, the term "horizontal" is intended to refer to a direction (e.g., anterior-posterior direction or lateral direction) generally perpendicular to the longitudinal axis of a spinal column of a patient.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

There are many types of spinal column disorders and abnormal curvatures of the spinal column including scoliosis (abnormal lateral curvature of the spine), kyphosis (abnormal forward curvature of the spine, usually in the thoracic spine), excess lordosis (abnormal backward curvature of the spine, usually in the lumbar spine), spondylolisthesis (forward displacement of one vertebra over another, usually in the lumbar or cervical spine), as well as other disorders caused by abnormalities, disease or trauma.

Figure 1B:
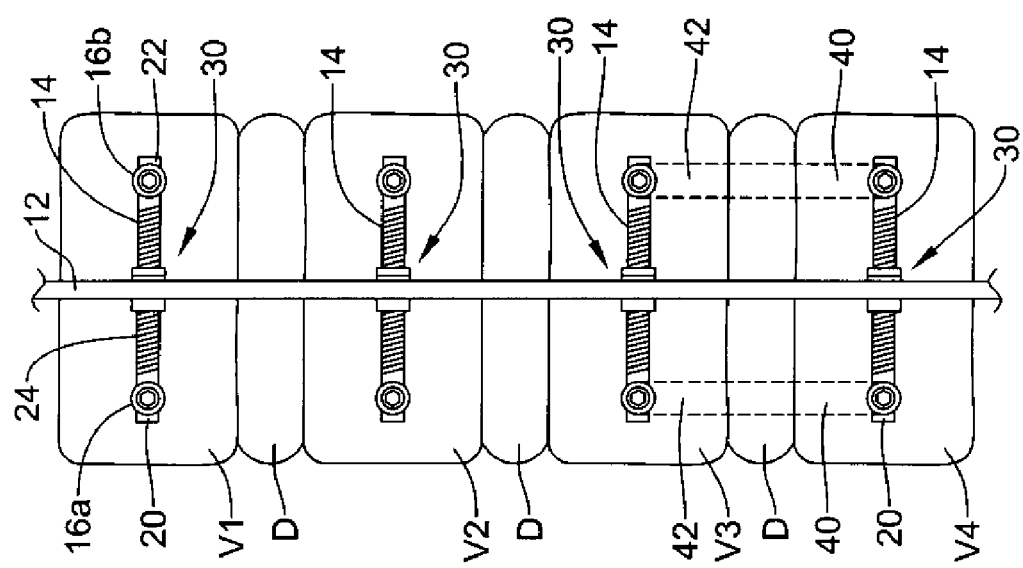
FIG. 1B shows the spinal segment of FIG. 1A subsequent to correcting an abnormal curvature of the spinal column.

FIGS. 1A and 1B are posterior views of a spinal column illustrating an exemplary assembly 10 for post-operatively treating an abnormal curvature of vertebrae of a spinal column. The assembly 10 may be installed on the posterior side of the spinal column, extending along a segment of the spinal column. Although showed installed on the posterior side of the spinal column, in some instances it may be desirable to install the assembly 10 on a lateral side of the spinal column or on the anterior side of the spinal column.

As used herein, a spinal segment is intended to refer to two or more vertebrae, the intervertebral disc(s) between the vertebrae and other anatomical elements between the vertebrae. For example, a spinal segment may include first and second adjacent vertebrae and the intervertebral disc located between the first and second vertebrae. In other embodiments, a spinal segment may include additional adjacent vertebrae and the intervertebral disc(s) located between the vertebrae. Two adjacent vertebrae and the anatomical structures between the adjacent vertebrae may be considered one level of the spinal column. Thus, in some embodiments the assembly 10 may span one, two, three, four, five, six, seven, eight, nine, ten or more vertebral levels as desired. For instance, FIGS. 1A and 1B illustrate three levels of the spinal column.

A spinal segment including four vertebral levels is illustrated in FIGS. 1A and 1B. The vertebrae shown in FIGS. 1A and 1B are provided for illustrative purposes, while omitting some anatomical features of the vertebrae. For example, transverse processes, spinous processes, and/or facet joints which may be associated with one or more of the vertebrae have been omitted for clarity. The vertebrae shown in FIGS. 1A and 1B may be located in the cervical region, thoracic region, lumbar region, and/or the sacral region of the spinal column. The illustrated spinal segment includes a first vertebra V1, a second vertebra V2 adjacent to and inferior to the first vertebra, a third vertebra V3 adjacent to and inferior to the second vertebra, and a fourth vertebra V4 adjacent to and inferior to the third vertebra V3. In some embodiments, the spinal segment may include the sacrum. Also illustrated are the intervertebral discs D located between adjacent vertebrae.

In other embodiments, the spinal segment may include additional or fewer vertebrae depending on the abnormality to be treated.

As shown in FIG. 1A, the spinal column is illustrated as having an abnormal curvature, illustrated as an abnormal lateral curvature, which may be consistent with the abnormal spinal curvature of a patient diagnosed with scoliosis. It is understood, however, that in some instances, the assembly 10 may be used to correct other types of abnormal curvatures of the spinal column.

The assembly 10 may include an elongate member 12 extending generally vertically along a posterior side of the spinal column (i.e., along the longitudinal axis of the spinal column), and may extend from a superiormost vertebra of the spinal segment to an inferiormost vertebra of the spinal segment. One or more additional vertebrae may be located between the superiormost vertebra and the inferiormost vertebra in some embodiments. In some embodiments one or more spinous processes, or other anatomical structures of the vertebrae, may need to be removed or modified when installing the elongate member 12 along the spinal segment to provide access, clearance, or otherwise accommodate installation of the assembly 10.

The elongate member 12 may be of any desired size, shape, length, rigidity and/or flexibility. Some suitable configurations of the elongate member 12 are discussed later herein. However, it is noted that other configurations of the elongate member 12 are contemplated and may be chosen if desired. The elongate member 12 may be formed of a rigid material having a rigidity to withstand applied forces without appreciable deflection while installed on the spinal column. In some embodiments, the elongate member 12 may be formed of a material which allows for a desired degree of bending or deflection of the elongate member 12.

The elongate member 12 may be connected to the superiormost vertebra, the inferiormost vertebra and/or one or more additional vertebrae located between the superiormost vertebra and the inferiormnost vertebra. For example, as shown in FIGS. 1A and 1B, the elongate member 12 may be connected to the first vertebra V1, the second vertebra V2, the third vertebra V3 and/or the fourth vertebra V4 of the vertebral segment. For example, as shown in FIG. 1A, the elongate member 12 may be connected to the vertebrae of the vertebral segment via a transverse member 14 associated with each of the first, second, third and fourth vertebrae V1, V2, V3, V4. In some embodiments, however, the elongate member 12 may be connected to one or more of the vertebrae of the vertebral segment in another fashion, for example, with one or more threaded fasteners (e.g., pedicle screws) secured directly to the elongate member 12.

The plurality of transverse members 14 of the assembly 10 may extend generally perpendicular to the elongate member 12 in a generally horizontal direction. In some embodiments, for example, a transverse member 14 may be associated with one or more of the vertebrae of the spinal segment, and/or may be associated with each of the vertebrae of the spinal segment. As shown in FIG. 1A, each of the transverse members 14 may be secured to a respective one of the vertebrae with one or more, or a plurality of fasteners 16 (e.g., pedicle screws). For instance, a first fastener 16a may be anchored to a first pedicle, or other anatomical region, of the first vertebra V1 and a second fastener 16b may be anchored to a second pedicle, or other anatomical region, of the first vertebra V1. In some embodiments, the fasteners 16 may be top loading pedicle screws including a threaded portion screwed into the vertebra and a U-shaped head portion configured to receive an end region of the transverse member 14. Set screws 18, or other locking members, such as other threaded members threadedly engaging a threaded portion of the fastener 16, may be used to secure the transverse member 14 to the head portion of the fastener 16. Some exemplary top loading pedicle screws which may be suitable for the assembly 10 are disclosed in U.S. Pat. No. 7,335,201 and U.S. Pat. App. Pub. Nos. 2006/0089643 and 2006/0052786, each of which is incorporated herein by reference.

The transverse member 14, may include a first end region 20 proximate the first fastener 16a, a second end region 22 proximate the second fastener 16b, and a central region 24 between the first end region 20 and the second end region 22. At least a portion of the transverse member 14 may be threaded. For example, the central region 24 of the transverse member 14 may be a threaded region of the transverse member 14 having threads helically arranged along a length of the transverse member 14. In some embodiments, the helically threaded central region 24 may include a first threaded portion extending laterally from a first side of the elongate member 12 and a second threaded portion extending laterally from a second side of the elongate member 12. The threaded central region 24 may include threads extending continuously in a first helical direction along the threaded region throughout the first and second threaded portions from a first end of the threaded central region 24 to a second end of the central threaded region 24.

In some embodiments, the end regions 20, 22 may also be threaded. However, in some embodiments, the end regions 20, 22 of the transverse member 14 may have a smooth outer surface, a grooved outer surface, a knurled outer surface, or other non-threaded outer surface, for example. The end regions 20, 22 of the transverse member 14 may be secured to the fasteners 16 such that the transverse member 14 extends from the first fastener 16a to the second fastener 16b with the central region 24, which may be an externally threaded region, positioned between the first fastener 16a and the second fastener 16b.

In some instances, the transverse member 14, secured to the first vertebra V1, or at least the threaded portion of the transverse member 14 may extend across the posterior side of the vertebral column between the fasteners 16 in a generally horizontal fashion. In a similar fashion, each of the other vertebrae of the vertebral segment may include a transverse member 14 and associated fasteners 16 securing the transverse member 14 to the respective vertebra, such as to the pedicles or other anatomical regions of the vertebra.

The assembly 10 may additionally include a coupler 30 coupling the elongate member 12 to the transverse member 14. The coupler 30 may include a stationary portion 32 attached, secured and/or fixed to the elongate member 12 and an actuatable portion 34 actuatable with respect to the stationary portion 32. For example, the actuatable portion 34 may include a rotating member 36 which may be rotatable relative to the stationary portion 32. In some embodiments, the rotating member 36 may be positioned on the transverse member 14 at a location intermediate the first and second ends of the threaded central region 24 of the transverse member 14.

As discussed further herein, actuation of the actuatable portion 34 may move the transverse member 14 relative to the elongate member 12. For example, the rotating member 36 may include an internally threaded portion threadedly engaged with the externally threaded portion of the transverse member 14. Thus, rotation of the rotating member 36 may advance the transverse member 14 in a generally lateral direction relative to the elongate member 12 (e.g., in a direction generally perpendicular to the longitudinal axis of the elongate member 12), applying a corrective force to the vertebra by moving either the first end portion 20 of the transverse member 14 (and thus the first fastener 16a) toward the elongate member 12 and the second end portion 22 of the transverse member 14 (and thus the second fastener 16b) away from the elongate member 12, or moving the first end portion 20 of the transverse member 14 (and thus the first fastener 16a) away from the elongate member 12 and the second end portion of the transverse member 14 (and thus the second fastener 16b) toward the elongate member 12.

Additional transverse members 14 are shown attached to each of the second vertebra V2, the third vertebra V3 and the fourth vertebra V4 of the vertebral segment with fasteners 16 in a similar fashion to that described above regarding the first transverse member 14 attached to the first vertebra V1. Namely, a second transverse member 14 is attached to the second vertebra V2, a third transverse member 14 is attached to the third vertebra V3, and a fourth transverse member 14 is attached to the fourth vertebra V4.

Additionally, each of the second, third and fourth transverse members 14 may be coupled to the elongate member 12 with a coupler 30 in a similar fashion to that described above regarding the coupler 30 coupling the first transverse member 14 to the elongate member 12.

In some embodiments, a stabilization system, such as a dynamic stabilization system 40, may also be installed on the spinal column. As shown in FIG. 1A, a dynamic stabilization system 40 is shown installed between the third vertebra V3 and the fourth vertebra V4 on either side of the spine. One example of a dynamic stabilization system which may be used is the DYNESYS® Spinal Fixation System, available from Zimmer Spine, Inc. of Edina, Minn. Such dynamic stabilization systems 40 may include a flexible spacer 42 positioned between two fasteners 16 installed in adjacent vertebrae of the spine. A flexible cord (not shown), extending through the flexible spacer may be tensioned between the fasteners 16. The combination of the flexible spacer and the flexible cord may provide dynamic support of the spinal column in both extension and flexion.

The assembly 10 may provide a controllable gradual corrective force to the vertebrae of the spinal segment of the spinal column to correct the abnormal curvature of the spinal column. The corrective forces exerted on the vertebrae may initially be applied during installation of the assembly 10 during a surgical operation, and subsequently the corrective forces may be progressively increased, decreased, adjusted, maintained or otherwise controlled post-operatively without Arther invasive surgery. Thus, instead of applying a full correction force at the time of installation of the assembly 10, which may be injurious to the spinal column, the assembly 10 allows for corrective forces to be gradually applied to the vertebrae in order to allow gradual movement of the vertebrae over a period of time to realign the misaligned vertebrae toward the longitudinal axis of the spinal column, thus partially or fully correcting the abnormal curvature of the spine. This gradual movement imparted by the assembly 10 may reduce the magnitude of forces applied to tissues of the spine, allowing soft tissues and/or muscles of the spinal column the ability to gradually adjust to the corrective shifting of the vertebrae, attributed to the viscoelastic behavior of tissues of the spinal column.

Actuation of the actuatable portion 34 (e.g., the rotating member 36), resulting in movement of the transverse member 14, may exert a corrective force to the vertebra to which the transverse member 14 is secured to, in order to correct the abnormal curvature of the spinal column, drawing the vertebrae toward the sagittal plane of the patient. Periodic adjustments to the assembly 10, in which the rotating member 136 may be rotated a desired amount at each adjustment, may be performed post-operatively to provide gradual movement of the vertebrae. The elongate member 12 may apply a countering force to the transverse members 14 counteracting the corrective forces applied to the vertebrae by the transverse members 14.

The actuation portion 34 may be actuated with suitable actuation means. For example, the actuation portion 34 may be magnetically actuatable by a remote magnetic field positioned exterior of the patient's body. The magnetic field may rotate a magnet of the actuation portion 34, thereby rotating the rotating member 36. Rotational movement of the rotating member 36 may be converted to linear movement of the transverse member 14 through the rotating member 36 through the interaction of the external threads of the transverse member 14 and the internal threads of the rotating member 36. Such actuation means allows for adjustments to be made post-operatively, without the need to make further incisions or other invasive actions. Other actuation means, such as an inductive electrical actuator or a thermally actuated actuator may be used to actuate the actuation portion 34, and thus rotate the rotating member 36 of the coupler 30 to convert rotational motion to linear motion of the transverse members 14.

The actuation portion 34 of the coupler 30 at each vertebra may be individually actuated to independently move the respective transverse member 14 of the desired vertebra with respect to the elongate member 12. Thus, during post-operative adjustment of the assembly 10, it may be determined that the first transverse member 14, connected to the first vertebra V1, may need to be laterally moved a first amount, thereby applying a first force to the first vertebra V1; the second transverse member 14, connected to the second vertebra V2, may need to be laterally moved a second amount, thereby applying a second force to the second vertebra V2; the third transverse member 14, connected to the third vertebra V3, may need to be laterally moved a third amount, thereby applying a third force to the third vertebra V3; and the fourth transverse member 14, connected to the fourth vertebra V4, may need to be laterally moved a fourth amount, thereby applying a fourth force to the fourth vertebra V4.

Furthermore, in some embodiments, the direction of movement of one or more of the transverse members 14 may be opposite to the direction of one or more of the remainder of the transverse members 14. For example, the transverse members 14 of the first and second vertebrae V1, V2 may be moved in a first lateral direction, and the transverse members 14 of the third and fourth vertebrae V3, V4 may be moved in a second lateral direction opposite the first lateral direction.

Evaluation of progress toward correcting the abnormal curvature may be made periodically and further adjustments to tension placed at individual levels of the spinal column by the assembly 10 performed. For example, X-rays may indicate that further adjustment of one or more of the transverse members 14 through rotation of the rotating member 36 of the associated coupler 30 may need to be made to draw one or more of the vertebrae further toward the longitudinal axis of the spinal column. These adjustments may be made post-operatively and non-invasively as desired until a desired or acceptable level of correction has been achieved.

FIG. 1B shows the spinal segment of the spinal column in which the abnormal curvature has been fully corrected over a period of time. As shown in FIG. 1B, tension placed on the vertebrae by the assembly 10 may draw the vertebrae into vertical alignment, such that the vertebrae are aligned, or more closely aligned, along the longitudinal axis of the spinal column.

Figure 2A:
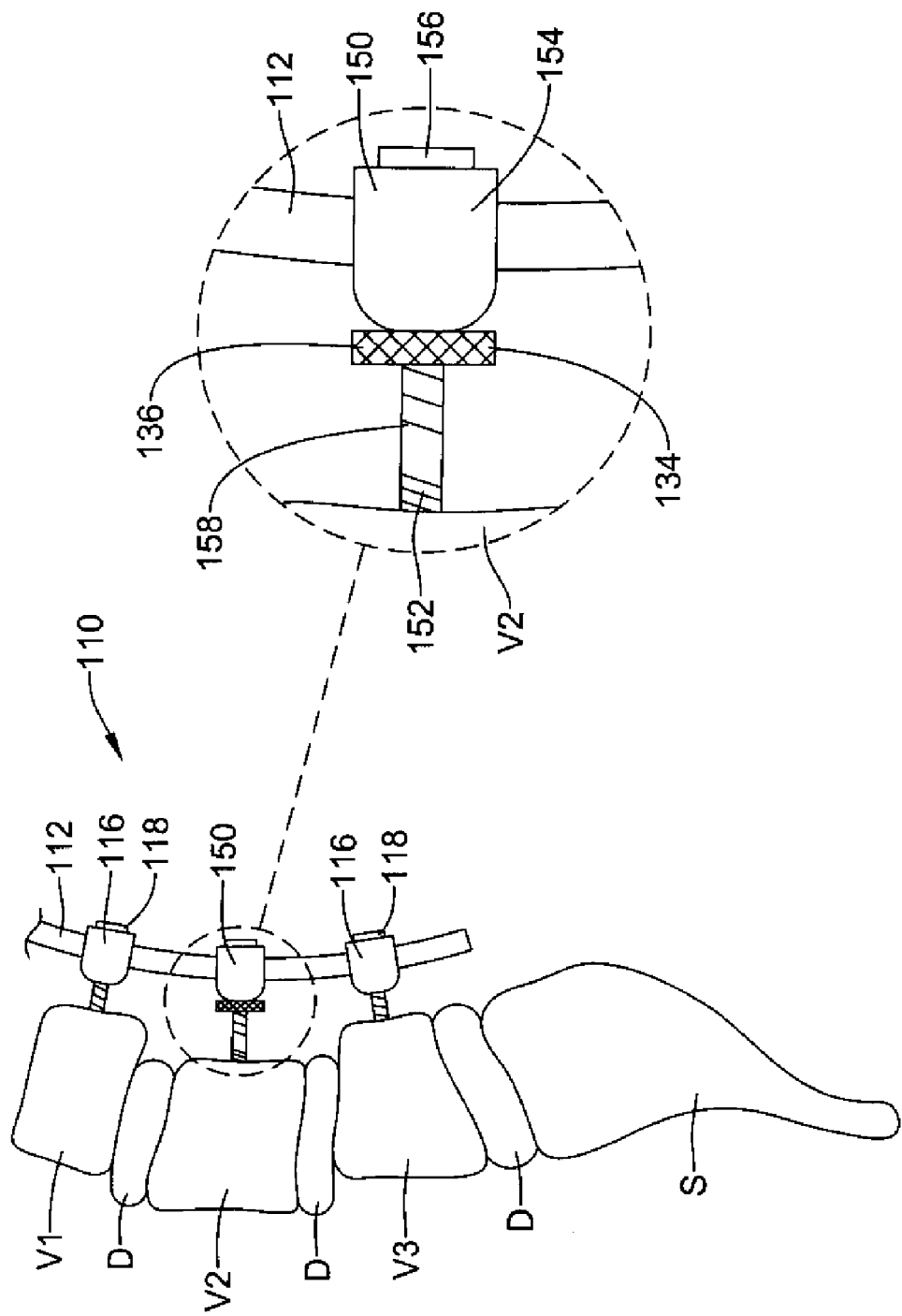
FIG. 2A shows another illustrative embodiment of an assembly for correcting an abnormal curvature of a spinal column.
Figure 2B:
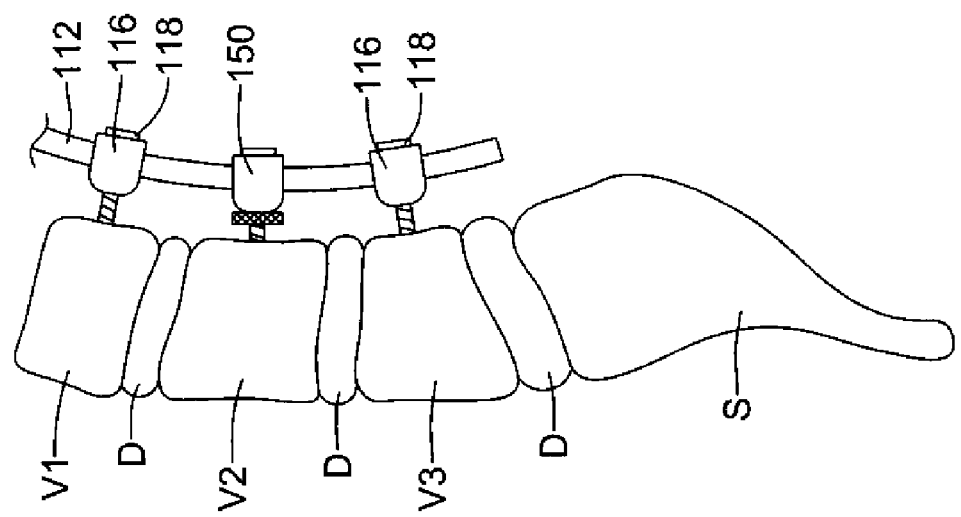
FIG. 2B shows the spinal segment of FIG. 2A subsequent to correcting an abnormal curvature of the spinal column.

Another exemplary embodiment of an assembly 110 for correcting an abnormal curvature of a spinal column is shown in FIGS. 2A and 2B. As shown in FIG. 2A, the spinal column is illustrated as having an abnormal curvature, illustrated as an abnormal forward displacement of one vertebra over another, which may be consistent with the abnormal spinal curvature of a patient diagnosed with spondylolisthesis. It is understood, however, that in some instances, the assembly 110 may be used to correct other types of abnormal curvatures of the spinal column.

As shown in FIG. 2A, the spinal segment may include a first vertebra V1, a second vertebra V2 and a third vertebra V3. The second vertebra V2 may be abnormally displaced anterior of a normal position relative to the adjacent vertebrae V1, V3. The vertebrae shown in FIGS. 2A and 2B are provided for illustrative purposes, while omitting some anatomical features of the vertebrae. For example, transverse processes, spinous processes, and/or facet joints which may be associated with one or more of the vertebrae have been omitted for clarity. Furthermore, although the vertebrae are shown as being located in the lumbar region, it is contemplated that the assembly 110 may be installed in the cervical region, thoracic region, lumbar region, and/or the sacral region of the spinal column.

The assembly 110 may include an elongate member 112 extending generally vertically along a posterior side of the spinal column (i.e., along the longitudinal axis of the spinal column), and may extend from a superiormost vertebra of the spinal segment to an inferiormost vertebra of the spinal segment. One or more additional vertebrae may be located between the superiormost vertebra and the inferiormost vertebra in some embodiments. In some embodiments one or more spinous processes, or other anatomical structures of the vertebrae, may need to be removed or modified when installing the elongate member 112 along the spinal segment to provide access, clearance, or otherwise accommodate installation of the assembly 110.

The elongate member 112 may be of any desired size, shape, length, rigidity and/or flexibility. Some suitable configurations of the elongate member 112 are discussed later herein. However, it is noted that other configurations of the elongate member 112 are contemplated and may be chosen if desired. The elongate member 112 may be formed of a rigid material having a rigidity to withstand applied forces without appreciable deflection while installed on the spinal column.

The elongate member 112 may be connected to the superiormost vertebra, the inferiormost vertebra and/or one or more additional vertebrae located between the superiormost vertebra and the inferiormost vertebra. For example, as shown in FIGS. 2A and 213, the elongate member 112 may be connected to the first vertebra V1, the second vertebra V2, and/or the third vertebra V3 of the vertebral segment. For example, as shown in FIG. 2A, the elongate member 112 may be connected to the vertebrae of the vertebral segment via one or more threaded fasteners (e.g., pedicle screws) secured or anchored to the respective vertebrae.

In some embodiments, the elongate member 112 may be connected to the first vertebra V1 with one or more fasteners 116 which maintains a constant distance between the elongate member 112 and the first vertebra V1, and the elongate member 112 may be connected to the third vertebra V3 with one or more fasteners 116 which maintains a constant distance between the elongate member 112 and the third vertebra V3.

For instance, one or more fasteners 116 may be anchored to the pedicles, or other anatomical regions, of the first vertebra V1, and one or more fasteners 116 may be anchored to the pedicles or other anatomical regions, of the third vertebra V3. In some embodiments, the fasteners 116, as described above, may be top loading pedicle screws including a threaded portion screwed into the vertebra and a U-shaped head portion configured to receive a portion of the elongate member 112 therethrough. Set screws 18, or other locking members, such as other threaded members threadedly engaging a threaded portion of the fastener 116, may be used to secure the elongate member 112 to the head portion of the fastener 116.

The assembly 110 may also include a connector 150 for connecting the elongate member 112 to the second, displaced vertebra V2. The connector 150 may include a first portion moveable relative to a second portion. For example, the first portion may include a threaded end region 152 for anchoring the connector 150 to the vertebra, and the second portion may include a head region 154 for securing the connector 150 to the elongate member 112. For example, the head region 154 may include a U-shaped portion defining a channel for receiving the elongate member 112 therethrough. A set screw 156, or other locking member, such as another threaded member threadedly engaging a threaded portion of the head region 154 may be used to secure the elongate member 112 to the head region 154 of the connector 150. The connector 150 may be configured such that the head region 154 is moveable (e.g., axially translatable in the direction of the longitudinal axis of the threaded end region 152) relative to the threaded end region 152.

The connector 150 may also include an actuatable member 134, such as a rotating member 136. The rotating member 136 may be rotatably coupled to the second portion, such as the head region 154 of the connector 150. The rotating member 136 may include a threaded portion, such as an internally threaded portion, threadedly engaged with a threaded portion 158, such as an externally threaded portion, of the first portion of the connector 150. In some embodiments, the threaded portion 158 may be distinct from the threaded end region 152 of the connector 150 anchored to the vertebra. Actuation of the actuatable member 134, such as rotation of the rotating member 136 may move the head region 154 toward or away from the threaded end region 152 by converting rotational movement of the rotating member 136 to linear movement of the first portion of the connector 150 toward or away from the second portion of the connector 150, thus drawing the second vertebra V2 toward the elongate member 112 and toward a normal position.

The actuatable member 134 may be actuated with suitable actuation means. For example, the actuatable member 134 may be magnetically actuatable by a remote magnetic field positioned exterior of the patient's body. The magnetic field may rotate a magnet of the actuatable member 134, thereby rotating the rotating member 136. Rotational movement of the rotating member 136 may be converted to linear movement of the first portion of the connector 150 relative to the second portion of the connector 150 through the rotating member 136 through the interaction of the threaded portion 158 of the first portion of the connector 150 and the threaded portion of the rotating member 136. Such actuation means allows for adjustments to be made post-operatively, without the need to make further incisions or other invasive actions. Other actuation means, such as an inductive electrical actuator or a thermally actuated actuator may be used to actuate the actuatable member 134, and thus rotate the rotating member 136 of the connector 150 to convert rotational motion to linear motion of the connector 150.

The assembly 110 may provide a controllable gradual corrective force to the vertebrae of the spinal segment of the spinal column to correct the abnormal curvature of the spinal column. The corrective forces exerted on the vertebrae may initially be applied during installation of the assembly 110 during a surgical operation, and subsequently the corrective forces may be progressively increased, decreased, adjusted, maintained or otherwise controlled post-operatively without further invasive surgery. Thus, instead of applying a full correction force at the time of installation of the assembly 110, which may be injurious to the spinal column, the assembly 110 allows for corrective forces to be gradually applied to the vertebrae in order to allow gradual movement of the vertebrae over a period of time to realign the misaligned vertebrae toward their normal curvature, thus partially or fully correcting the abnormal curvature of the spine. This gradual movement imparted by the assembly 110 may reduce the magnitude of forces applied to tissues of the spine, allowing soft tissues and/or muscles of the spinal column the ability to gradually adjust to the corrective shifting of the vertebrae, attributed to the viscoelastic behavior of tissues of the spinal column.

Actuation of the actuatable member 134 (e.g., the rotating member 136), resulting in movement of the second vertebra V2 toward the elongate member 112, may exert a corrective force to the second vertebra V2 to which the threaded end region 152 of the connector 150 is secured to, in order to correct the abnormal curvature of the spinal column, drawing the vertebrae toward the elongate member 112. Periodic adjustments to the assembly 110, in which the rotating member 136 may be rotated a desired amount at each adjustment, may be performed post-operatively to provide gradual movement of the vertebrae. The elongate member 112, which is connected to adjacent vertebrae V1, V3 with fasteners 116, may apply a countering force to the adjacent vertebrae V1, V3 counteracting the corrective forces applied to the second vertebra V2 by the connector 150.

Evaluation of progress toward correcting the abnormal curvature may be made periodically and further adjustments to tension placed on the displaced vertebra V2 of the spinal column by the assembly 10 performed. For example, X-rays may indicate that further adjustment of the connector 150 through rotation of the rotating member 136 of the connector 150 may need to be made to draw the second vertebra V2 further toward the elongate member 112, and into correct alignment with the adjacent vertebrae V1, V3. These adjustments may be made post-operatively and non-invasively as desired until a desired or acceptable level of correction has been achieved.

FIG. 2B shows the spinal segment of the spinal column in which the abnormal curvature has been fully corrected over a period of time. As shown in FIG. 2B, tension placed on the vertebrae by the assembly 10 may draw the second vertebra V2 into alignment with the adjacent vertebrae V1, V3, such that the vertebrae follow a normal curvature, or a more normal curvature, such as a normal lordotic curvature of the spine, for example.

Figure 3:
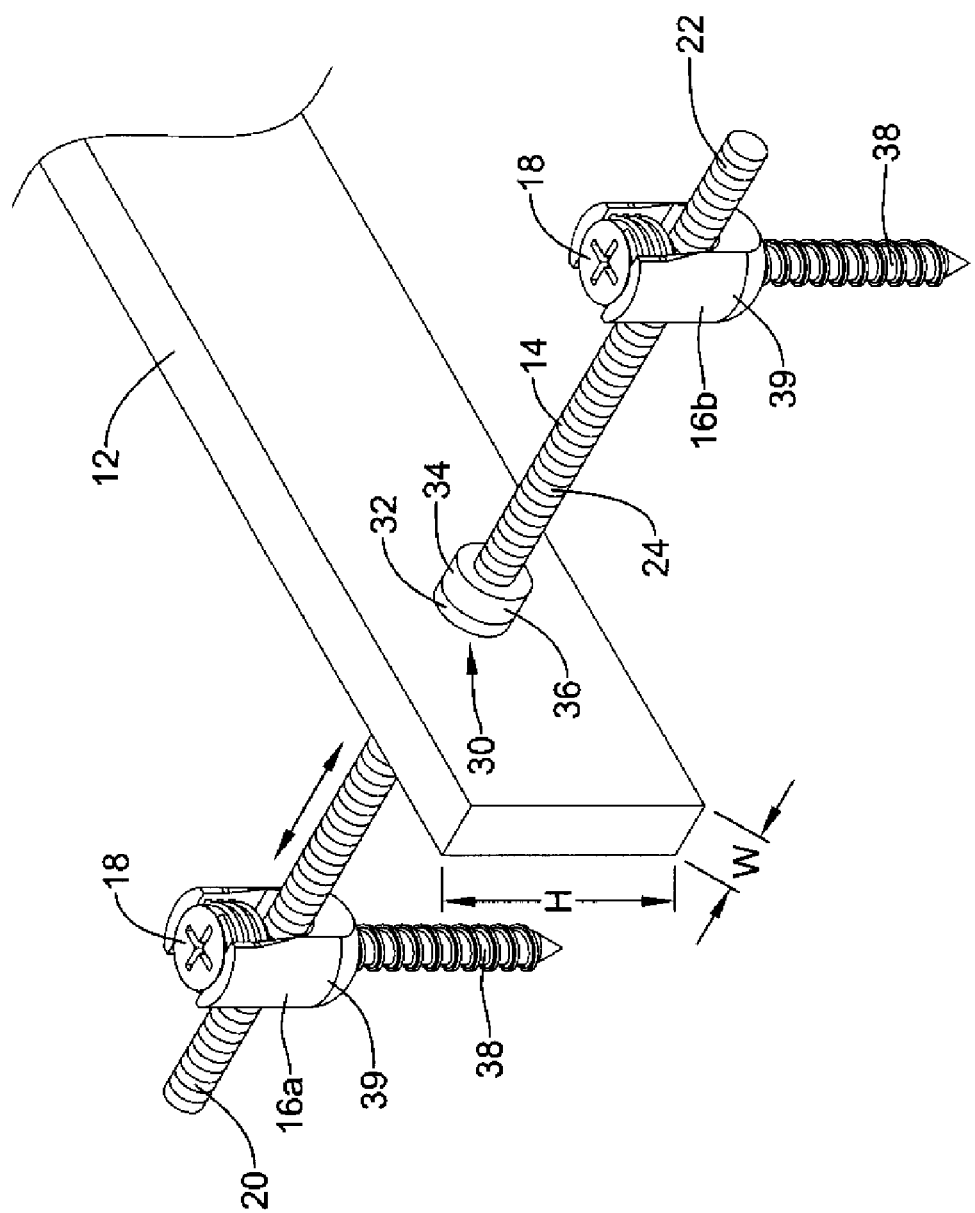
FIG. 3 is a perspective view of an exemplary embodiment of an assembly for correcting an abnormal curvature of a spinal column.

Several variations of components of the assembly 10 and/or the assembly 110 are shown in FIGS. 3-11. As shown in FIG. 3, the transverse member 14 may extend through the coupler 30 and the elongate member 12 from a first fastener 16a to a second fastener 16b. For example, the elongate member 12 may include an opening (not shown) through which the transverse member 14 may extend from one side of the elongate member 12 to a second side of the elongate member 12.

The coupler 30 may be attached to the elongate member 12. For example, the stationary portion 32 of the coupler may be secured, fixed and/or attached to the elongate member 12 proximate the opening such that the transverse member 14, which may extend through a bore of the coupler 30 may extend through the opening of the elongate member 12. In come embodiments, the bore of the coupler 30 may be coaxial with the opening of the elongate member 12. Rotation of the rotating member 36 of the coupler 30 axially moves the transverse member 14 in a direction shown by arrows in FIG. 3, along the central axis of the bore of the coupler 30, which may be generally perpendicular to the longitudinal axis of the elongate member 12.

As shown in FIG. 3, the elongate member 12 of the assembly 10 may having a width W in the lateral direction which is less than the height H in the anterior-posterior direction. Such a configuration may provide greater resistance to bending in an anterior-posterior direction than in a lateral direction. However, in other embodiments, the width W and/or the height H of the elongate member 12, thus the second moment of area of the cross-section of the elongate member 12, may be changed to provide a desired amount of resistance to bending in an anterior-posterior direction and/or in a lateral direction.

Furthermore, exemplary fasteners 16, which may be used to secure the transverse member 14 to a vertebra are also shown in FIG. 3. The fasteners 16 may be top loading pedicle screws including a threaded portion 38 configured to be screwed into the vertebra and a U-shaped head portion 39 configured to receive an end region of the transverse member 14. Set screws 18 may be used to secure the transverse member 14 to the head portion 39 of the fastener 16 by securing an end region of the transverse member 14 in the channel defined by the U-shaped head portion 39.

A first fastener 16a is shown secured to the first end region 20 of the transverse member 14 and a second fastener 16b is shown secured to the second end region 22 of the transverse member 14. Rotation of the rotating member 36 may allow the elongate member 12 to travel back and forth along the central threaded region 24 between the first fastener 16a and the second fastener 16b, thus moving the elongate member 12 closer or further away from the fasteners 16 as desired.

Figure 4:
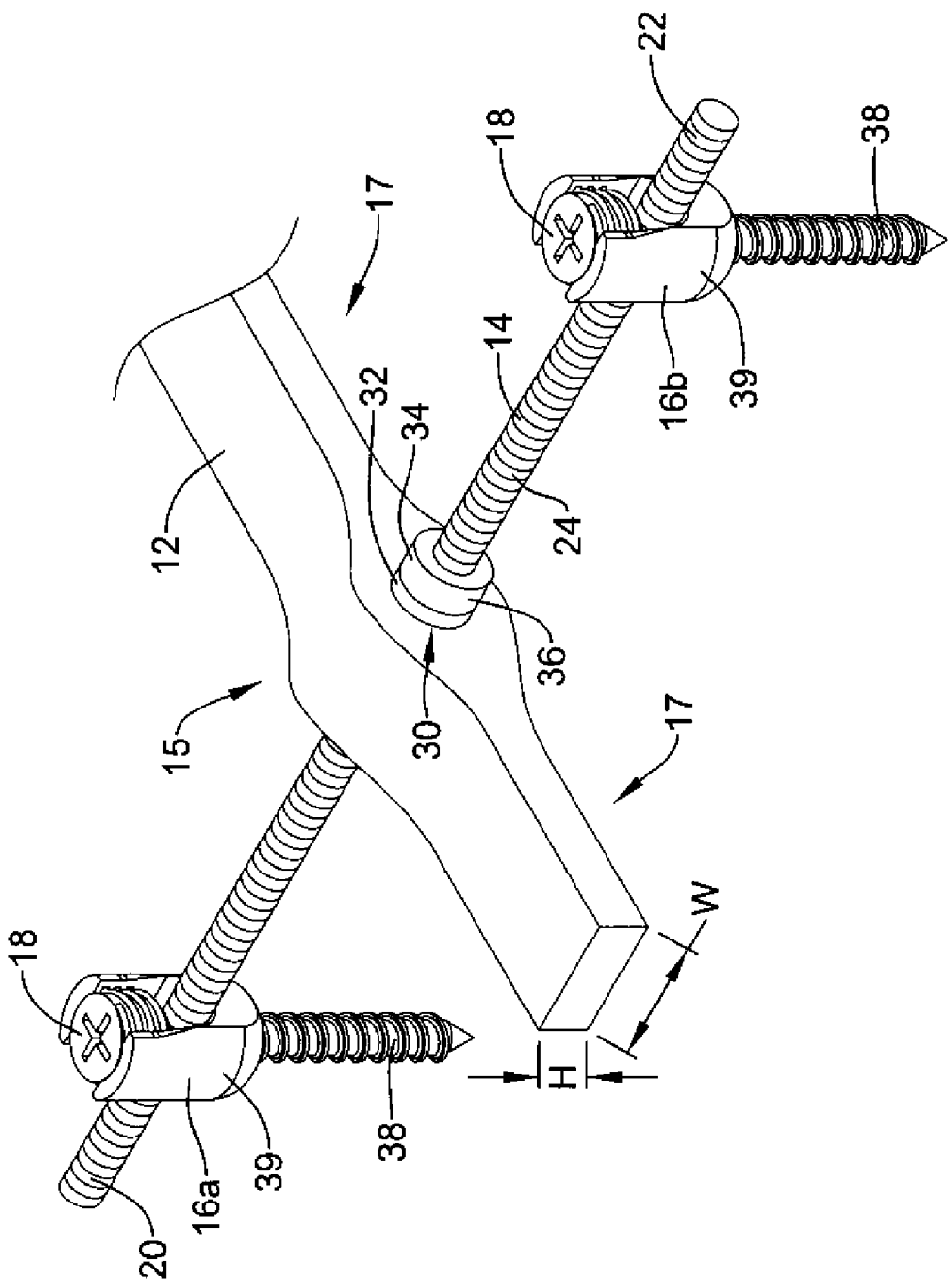
FIG. 4 is a perspective view another embodiment of an assembly for correcting an abnormal curvature of a spinal column.

FIG. 4 illustrates another embodiment of the assembly 10 similar to that shown in FIG. 3. As shown in FIG. 4, the elongate member 12 of the assembly 10 may having a width W in the lateral direction which is greater than the height H in the anterior-posterior direction. Such a configuration may provide greater resistance to bending in a lateral direction than in an anterior-posterior direction. Such a configuration may permit larger lateral forces to be exerted on the elongate member 10 while correcting the curvature of a spinal column. However, in other embodiments, the width W and/or the height H of the elongate member 12, thus the second moment of area of the cross-section of the elongate member 12, may be changed to provide a desired amount of resistance to bending in an anterior-posterior direction and/or in a lateral direction.

Because the height H of the elongate member 12 may be less than the diameter of the transverse member 14 and/or the bore through the coupler 30, the elongate member 12 may include a bulge region 15 through which the transverse member 14 extends and to which the coupler 30 is coupled to. Although only one bulge region 15 is shown in FIG. 4, the elongate member 12 may include a plurality of bulge regions 15 disposed intermediate reduced thickness regions 17 along the length of the elongate member 12. The bulge region 15 may include an opening (not shown) extending therethrough from a first side of the elongate member 12 to a second side of the elongate member 12. The transverse member 14 may extend through the opening of the bulge region 15 from the first side of the elongate member 12 to the second side of the elongate member 12.

The coupler 30 may be positioned such that the bore of the coupler 30, through which the transverse member 14 extends through, may be aligned with the opening of the bulge region 15, such that the transverse member 14 may be aligned with the opening of the bulge region 15.

Figure 5:
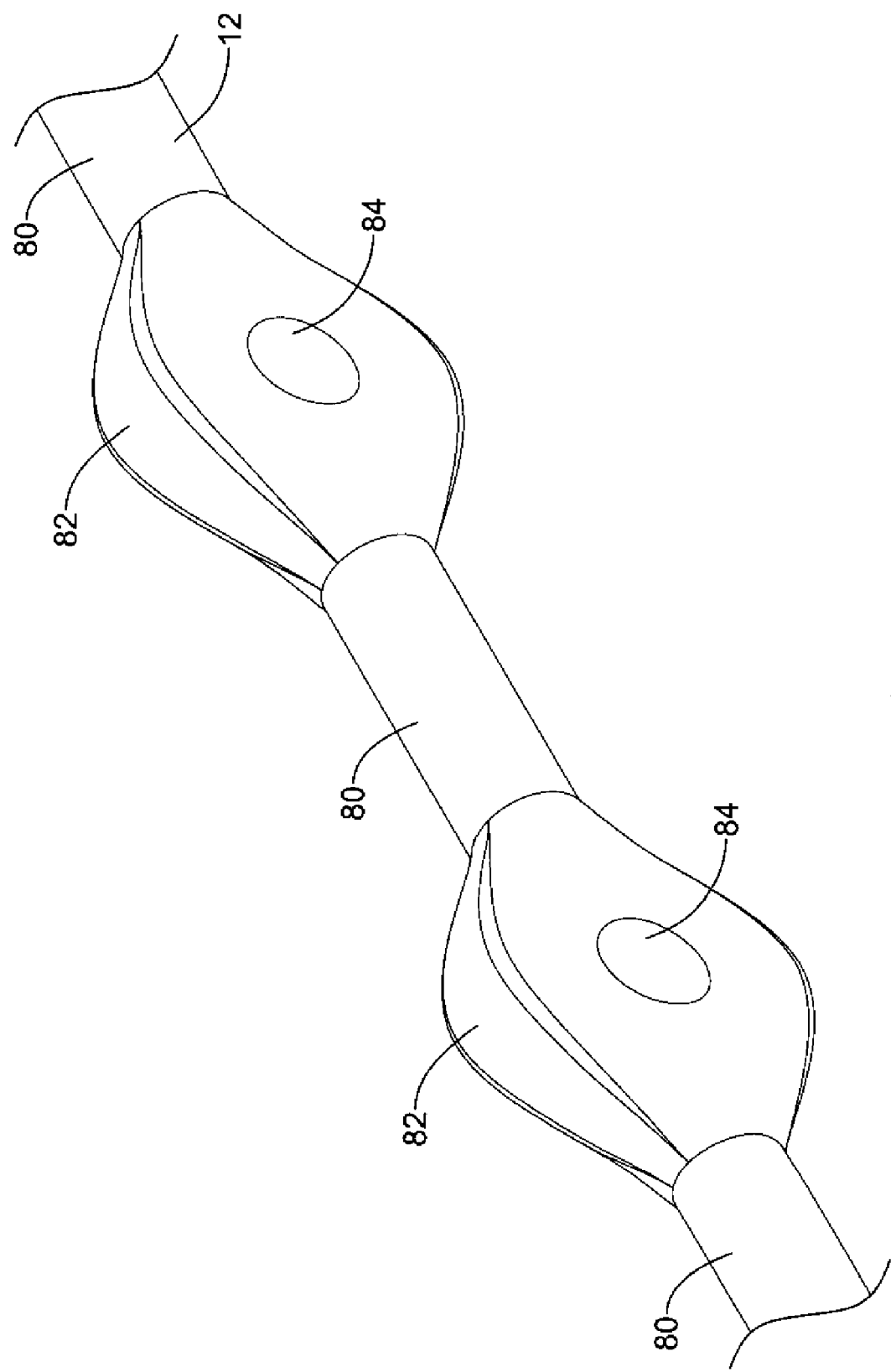
FIG. 5 is a perspective view of an exemplary embodiment of an elongate member of an assembly for correcting an abnormal curvature of a spinal column.

Another embodiment of the elongate member 12 of the assembly is shown in FIG. 5. Other components of the assembly 10, such as couplers 30 and transverse members 14, have been omitted from FIG. 5 in order to further illustrate features of the elongate member 12, such as openings 84 extending through portions of the elongate member 12 accommodating the couplers 30 and/or transverse members 14 of the assembly 10. However, it is understood that the couplers 30 and/or transverse members 14 described above may be assembled with the elongate member 12 of FIG. 5 to construct the assembly 10 shown in FIGS. 1A and 1B.

As shown in FIG. 5, the elongate member 12 may include cylindrical portions 80 and flattened portions 82 alternating along the length of the elongate member 12. The elongate member 12 may be bent or shaped to a desired curvature to suit a desired anatomical curvature of the spinal column and/or to navigate anatomical structures of the spinal column.

The flattened portions 82 may include openings 84, which may be similar to openings of the elongate member 12 discussed above regarding FIGS. 3 and 4. The openings 84, which may be located at each vertebral level of the spinal segment, may provide a passage through the elongate member 12 through which the transverse members 14 may extend through. Furthermore, the couplers 30 may be secured, attached and/or fixed to the elongate member 12 at the openings 84. For example, the couplers 30 may be pressed or screwed into the openings 84, welded, bolted, locked, or otherwise assembled with the elongate member 12, such that the bore through the coupler 30 is aligned with an opening 84 of a flattened portion 82 of the elongate member 12.

Figure 6:
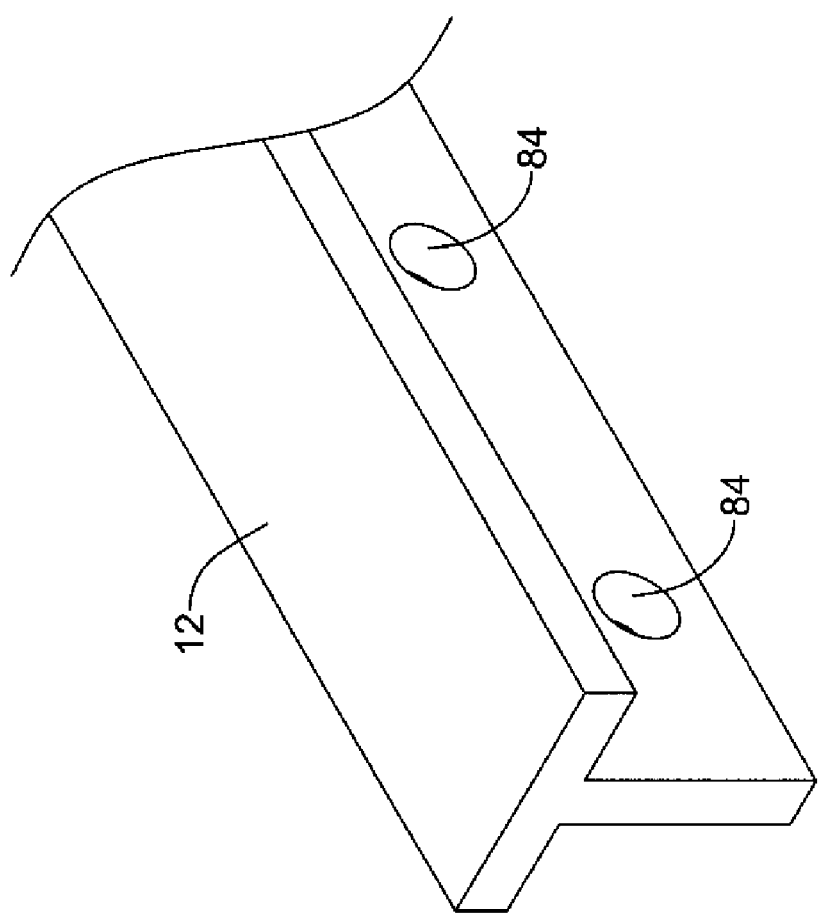
FIG. 6 is a perspective view of another exemplary embodiment of an elongate member of an assembly for correcting an abnormal curvature of a spinal column.

Another embodiment of the elongate member 12 of the assembly is shown in FIG. 6. Other components of the assembly 10, such as couplers 30 and transverse members 14, have been omitted from FIG. 6 in order to further illustrate features of the elongate member 12, such as openings 84 extending through portions of the elongate member 12 accommodating the couplers 30 and/or transverse members 14 of the assembly 10. However, it is understood that the couplers 30 and/or transverse members 14 described above may be assembled with the elongate member 12 of FIG. 6 to construct the assembly 10 shown in FIGS. 1A and 1B.

As shown in FIG. 6, the elongate member 12 may have a T-beam cross-section. It is noted that in other embodiments, the elongate member may have an I-beam, an H-beam, or other cross-section, if desired. The cross-section of the elongate member 12 may be chosen to increase the second moment of area of the elongate member 12 in one or more planes of bending in order to provide added resistance to bending to the elongate member 12 if desired.

The elongate member 12 is illustrated as including openings 84, which may be similar to openings of the elongate member 12 discussed above regarding FIGS. 3 and 5. The openings 84, which may be located at each vertebral level of the spinal segment, may provide a passage through the elongate member 12 through which the transverse members 14 may extend through. Furthermore, the couplers 30 may be secured, attached and/or fixed to the elongate member 12 at the openings 84. For example, the couplers 30 may be pressed or screwed into the openings 84, welded, bolted, locked, or otherwise assembled with the elongate member 12, such that the bore through the coupler 30 is aligned with an opening 84 of the elongate member 12.

Figure 7:
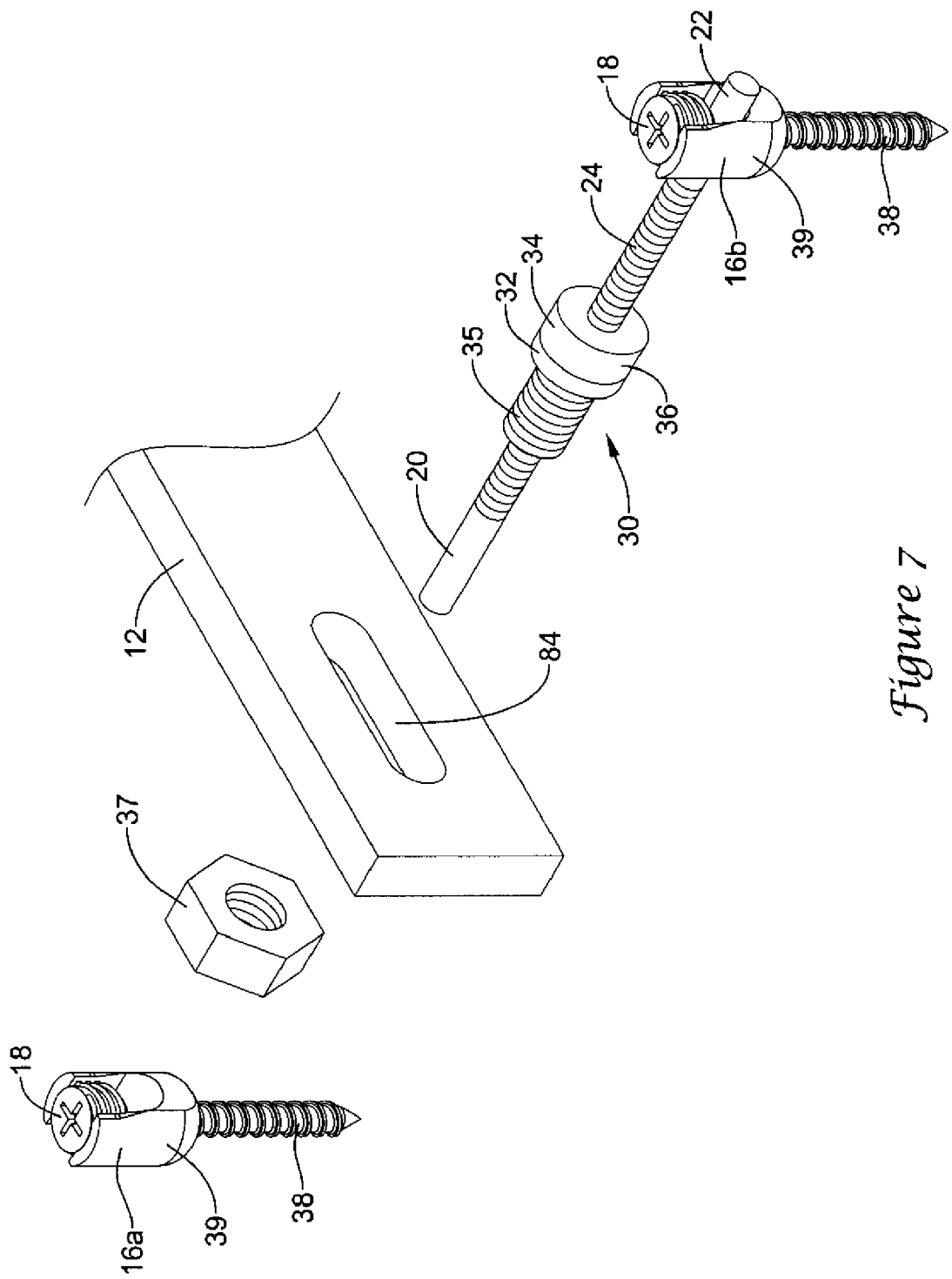
FIG. 7 is a perspective exploded view of another exemplary embodiment of an assembly for correcting an abnormal curvature of a spinal segment.

Another embodiment of components of the assembly 10 is illustrated in FIG. 7. As shown in FIG. 7, the elongate member 12 may include openings 84, one of which is shown, through which the transverse members 14 may extend through. The openings 84 may be elongated slots, allowing a range of adjustability of the position of the transverse member 14 along the longitudinal length of the elongate member 12.

Furthermore, as shown in FIG. 7, the transverse member 14 may extend through a bore of the coupler 30. The coupler 30 may be used to couple the transverse member 14 to the elongate member 12. The coupler 30 may include a stationary portion 32 attached, secured and/or fixed to the elongate member 12 and an actuatable portion 34 actuatable with respect to the stationary portion 32. For example, the actuatable portion 34 may include a rotating member 36 which may be rotatable relative to the stationary portion 32. The rotating member 36 may be rotatably coupled to the stationary portion 32 of the coupler 30. The rotating member 36 may include an internally threaded portion mating with the threaded portion of the transverse member 14.

Additionally, the coupler 30 may include a stem 35 configured to extend into and/or through the opening 84 of the elongate member 12. A threaded nut 37, or other fastener, may be positioned on the opposite side of the elongate member 12 to engage the stem 35, and thus secure or lock the coupler 30 to the elongate member 12. For instance, the internal threads of the nut 37 may be threadedly engaged with the externally threaded portion of the stem 35 to secure the elongate member 12 between a surface of the nut 37 and a surface of the stationary portion 32 of the coupler 30, which in some instances may be considered a flange. In other embodiments, the opening 84 may be a threaded opening configured to threadedly engage the threaded portion of the stem 35 of the coupler 30.

In the embodiment of FIG. 7, the stem 35 of the coupler 30 may be positioned at any one of several positions within the opening 84 along the longitudinal length of the elongated opening 84 (e.g., elongated slot) of the elongate member 12. Thus, the position of the transverse member 14 may be adjusted between a superiormost position and an inferiormost position within the extents of the opening 84 to accommodate placement of the transverse member relative to anatomical structures of the vertebral column. Once the transverse member 14 is properly positioned, the nut 37, or other fastener may secure the coupler 30 (and thus the transverse member 14) at a singular fixed location along the longitudinal axis of the elongate member 12.

Furthermore, exemplary fasteners 16, which may be used to secure the transverse member 14 to a vertebra are also shown in FIG. 7. The fasteners 16 may be top loading pedicle screws including a threaded portion 38 configured to be screwed into the vertebra and a U-shaped head portion 39 configured to receive an end region of the transverse member 14. Set screws 18 may be used to secure the transverse member 14 to the head portion 39 of the fastener 16 by securing an end region of the transverse member 14 in the channel defined by the U-shaped head portion 39.

A first fastener 16a is shown secured to the first end region 20 of the transverse member 14 and a second fastener 16b is shown which may be secured to the second end region 22 of the transverse member 14. Rotation of the rotating member 36 may allow the elongate member 12 to travel back and forth along the central threaded region 24 between the first fastener 16a and the second fastener 16b, thus moving the elongate member 12 closer or further away from the fasteners 16 as desired.

Figure 8:
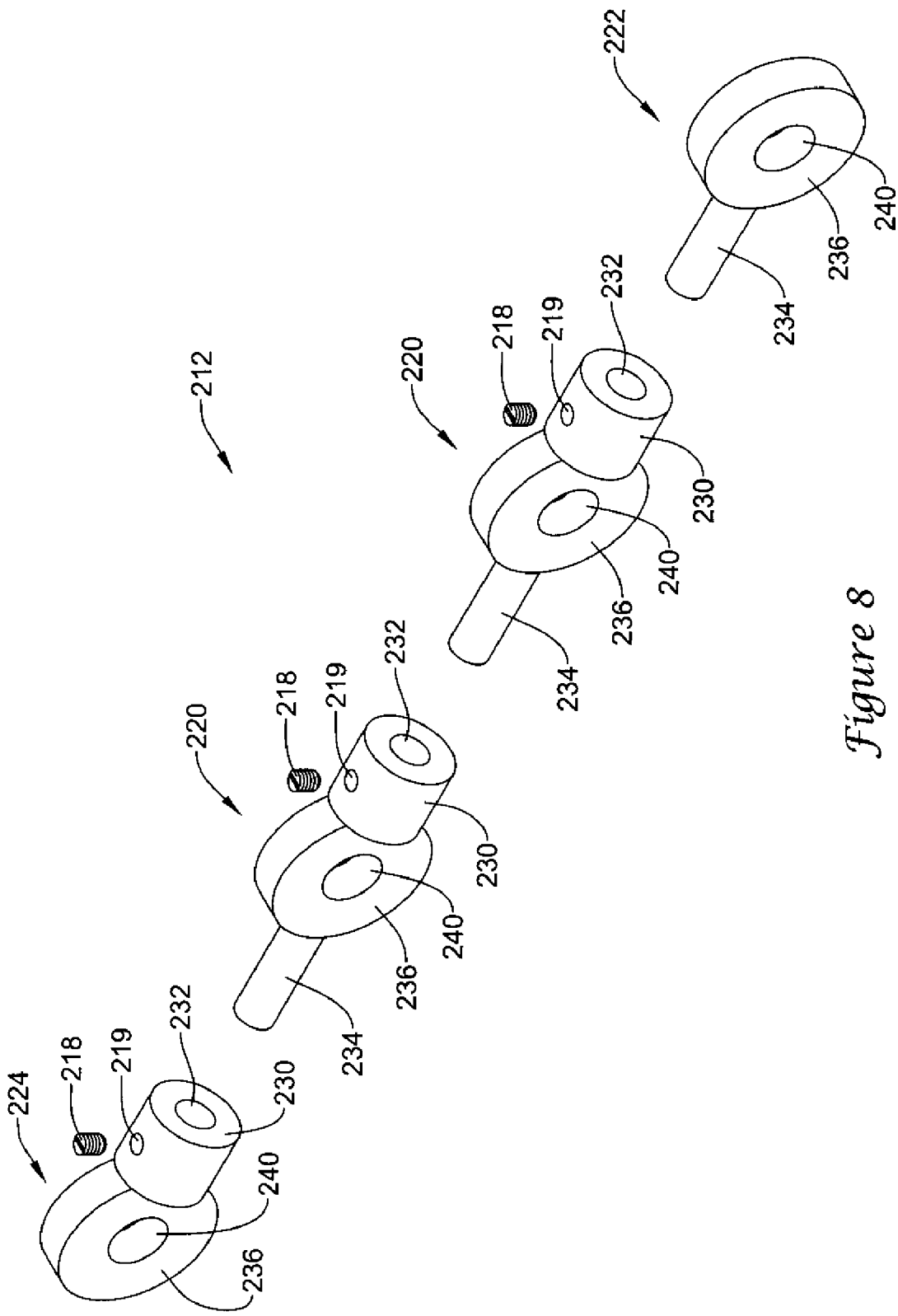
FIG. 8 is a perspective view of another exemplary embodiment of an elongate member of an assembly for correcting an abnormal curvature of a spinal column.

Another embodiment of an elongate member 212, similar to the elongate member 12 of the assembly 10 is shown in FIG. 8. Other components of the assembly 10, such as couplers 30 and transverse members 14, have been omitted from FIG. 8 in order to further illustrate features of the elongate member 212, such as openings 240 extending through portions of the elongate member 212 accommodating the couplers 30 and/or transverse members 14 of the assembly 10. However, it is understood that the couplers 30 and/or transverse members 14 described above may be assembled with the elongate member 212 of FIG. 8 to construct the assembly 10 shown in FIGS. 1A and 1B.

The elongate member 212 includes a plurality of segments 220, 222, 224 which may be coupled together to form the elongate member 212. For example, as shown, the elongate member 212 may include a first end segment 222, a second end segment 224, and one or more, or a plurality of intermediate segments 220 located between the first end segment 222 and the second end segment 224. Each of the segments 220, 222, 224 may include a coupling region 236 including an opening 240, or other structure for coupling with the couplers 30. In some embodiments, the coupling region 236 may be a flattened portion having one or more flat or planar surfaces, a disk shape, an annular shape or other desired configuration. However, in other embodiments the coupling region 236 may be of any other configuration for coupling the coupler 30 thereto.

The segments 220, 222, 224 may be configured such that the distance between the opening 240 of one segment 220, 222, 224 and the opening 240 of an adjacent segment 220, 222, 224 may be adjusted as desired. For example, each of the segments 220, 222, 224 may include a connector portion which may mate with a connector portion of an adjacent segment 220, 222, 224 to allow adjustment of the distance between the openings 240, and thus the overall longitudinal length of the elongate member 212. For instance, the first end segment 222 may include a post 234 extending from the coupling region 236 which may be slidably disposed in the bore 232 of the receiver 230 of the adjacent intermediate segment 220. Although the post 234, bore 232 and receiver 230 are shown as having circular cross-sections, it is noted that in other embodiments, one or more of the post 234, bore 232 and or receiver 230 may have another desired cross-section. The receiver 230 of the adjacent intermediate segment 220 may slidably receive the post 234 of the first end segment 222.

The intermediate segment 220 may include a set screw 218, or other fastener, threaded into a threaded bore 219 of the receiver 230. When the position of the post 234 of the first end segment 222 is in the desired position within the bore 232 of the receiver 230 (e.g., the desired distance between the opening 240 of the first end segment 222 and the opening 240 of the intermediate segment 220 in attained), the set screw 218 may be tightened against the post 234 to secure or lock the post 234 in the bore 232, preventing further sliding movement of the post 234 in the bore 232.

Similar adjustment may be attained between the openings 240 of the remainder of the segments 220, 222, 224. For example, each of the intermediate segments 220 may include a post 234 extending in a first direction and a receiver 230 extending in a second direction opposite the first direction. Thus, the post 234 of one segment 220, 222 may extend into the receiver 230 of an adjacent segment 220, 224. The second end segment 224, located at the opposite end of the elongate member 212 from the first end segment 222, may include a receiver 230 with an axial bore 232 for receiving the post 234 of an adjacent intermediate segment 220 therein. The interaction between the post 234 of one segment 220, 222 and the receiver 230 of an adjacent segment 220, 224 may allow the distances between openings 240 of the elongate member 212 to be adjusted to accommodate anatomical structures and/or specific dimensions of the spinal column of the patient (e.g., the longitudinal spacing of vertebrae of the spinal column).

Figure 9:
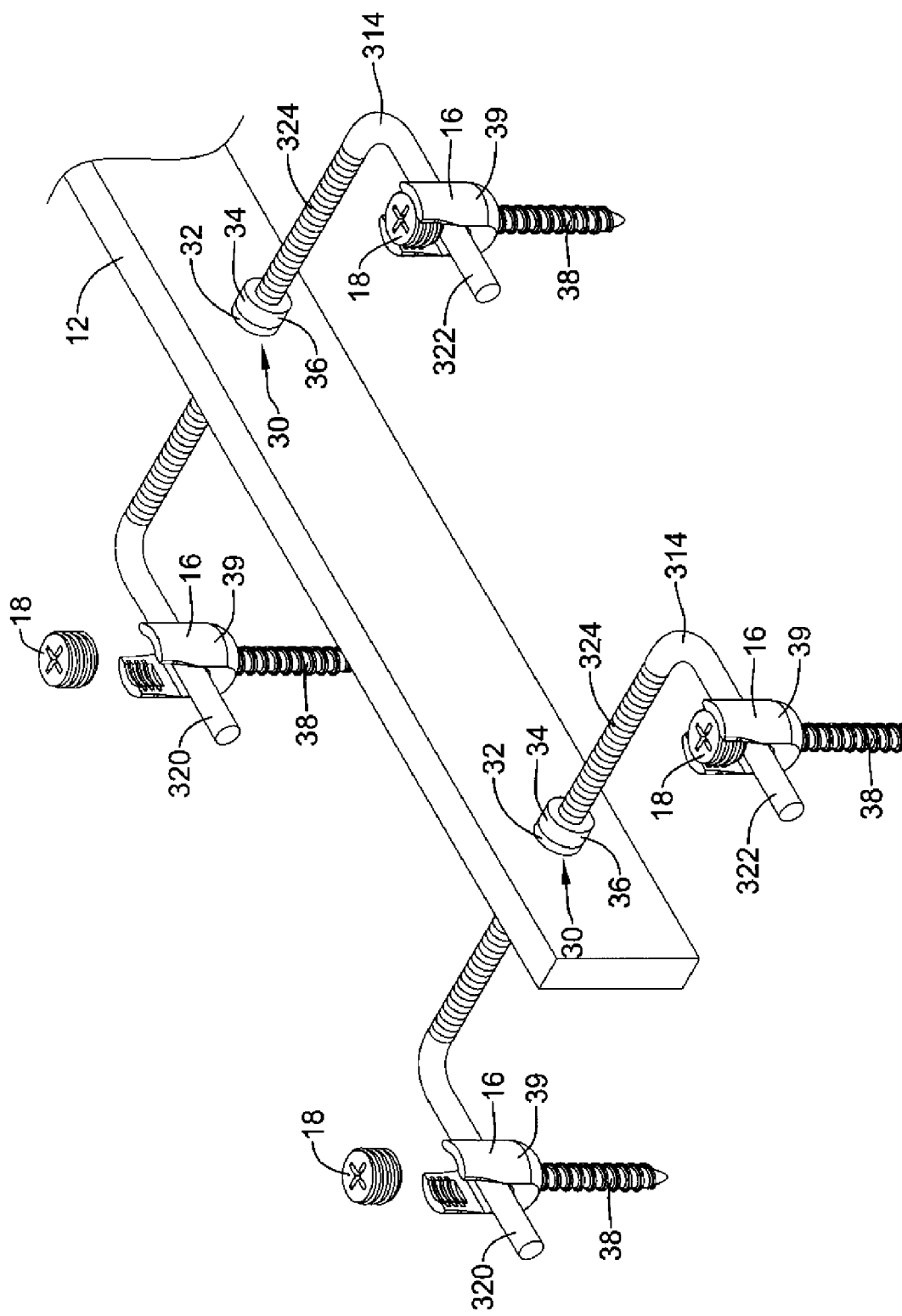
FIG. 9 is a perspective view of another exemplary embodiment of an assembly for correcting an abnormal curvature of a spinal segment.

FIG. 9 illustrates another embodiment of the assembly 10 of FIGS. 1A and 1B. The assembly includes an elongate member 12 and a plurality of transverse members 314 coupled to the elongate member 12 with couplers 30. The transverse member 314 may include a first end region 320, a second end region 322, and a central region 324 between the first end region 320 and the second end region 322.

At least a portion of the transverse member 314 may be threaded. For example, the central region 324 of the transverse member 314 may be a threaded region of the transverse member 314 having threads helically arranged along a length of the transverse member 314 which threadedly engage with the rotating member 36 of the coupler 30. Rotation of the rotating member 36 may allow the elongate member 12 to travel back and forth along the central threaded region 324 of the transverse member 314.

The first and second end regions 320, 322 may be positioned at an angle relative to the longitudinal axis of the central region 324 of the transverse member 314. For example, at least a portion of the first and second end regions 320, 322 may have a longitudinal axis perpendicular to the longitudinal axis of the central region 324.

Furthermore, exemplary fasteners 16, which may be used to secure the transverse member 314 to a vertebra are also shown in FIG. 9. The fasteners 16 may be top loading pedicle screws including a threaded portion 38 configured to be screwed into the vertebra and a U-shaped head portion 39 configured to receive an end region of the transverse member 314. Set screws 18 may be used to secure the transverse member 314 to the head portion 39 of the fastener 16 by securing an end region of the transverse member 314 in the channel defined by the U-shaped head portion 39.

First and second fasteners 16 are shown secured to the first end region 320 and the second end region 322 of the transverse member 314, respectively. In the configuration shown in FIG. 9, the end regions 320, 322 of the transverse member 314 may be adjusted axially within the channels of the fasteners 16 to accommodate adjustment of the assembly 10 on the vertebral column of the patient. Thus, the lateral position of the central region 324 of the transverse member 314 may be adjusted superiorly and/or inferiorly by axially moving the end regions 320, 322 of the transverse member 314 superiorly and/or inferiorly within the channels of the head portion 39 of the fasteners 16.

Figure 10:
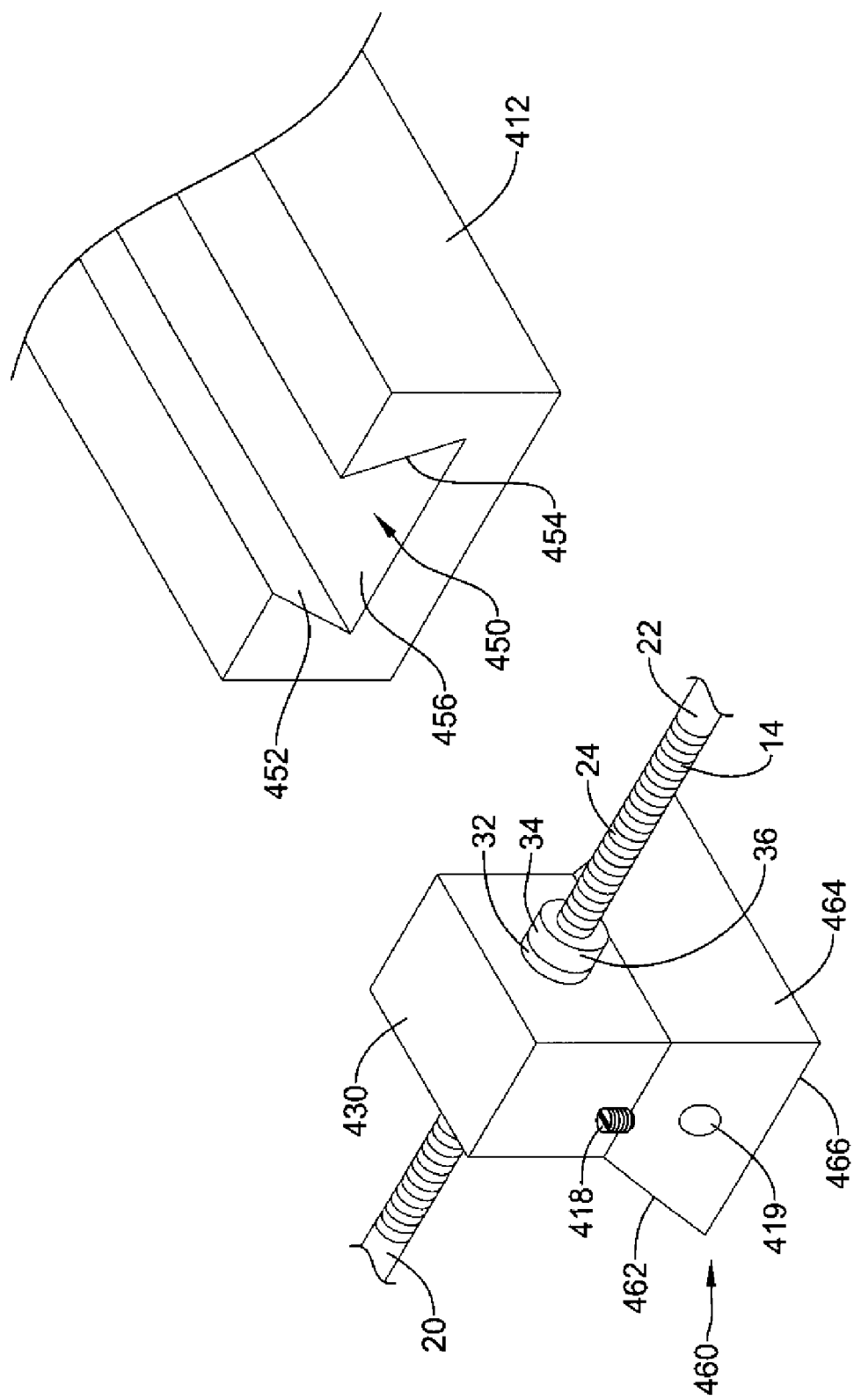
FIG. 10 is a perspective view of another exemplary embodiment of an assembly for correcting an abnormal curvature of a spinal segment.

Another embodiment of components of the assembly 10 is shown in FIG. 10. As illustrated, the assembly 10 may include an elongate member 412, which may be a variation of the elongate member 12 described above, extending along a posterior portion of the spinal column. The elongate member 412 may include a channel 450 extending along at least a portion of the length of the elongate member 412. In some embodiments, the channel 450 may extend from a superior end of the elongate member 412 to an inferior end of the elongate member 412. In some embodiments, the channel 450 may be of a dovetail configuration, having first and second sloping side walls 452, 454 sloping toward one another, and a bottom wall 456. The side walls 452, 454 may be configured such that the distance between the side walls 452, 454 is greater near the bottom wall 456 than near the opening between the side walls 452, 454. In other embodiments, the channel 450 may be shaped, sized, or otherwise configured, as desired.

The assembly may also include a coupler 430 having a body including a tenon 460 (e.g., a projecting portion) shaped, sized and/or configured to mate with the channel 450 of the elongate member 412. For example, the tenon 460 of the body of the coupler 430 may be slidably disposed in the channel 450 of the elongate member 412 such that the surface 462 of the coupler 430 is facing, parallel to, and/or in contact with the side wall 452 of the channel 450, the surface 464 of the coupler 430 is facing, parallel to, and/or in contact with the side wall 454 of the channel 450, and/or the surface 466 of the coupler 430 is facing, parallel to, and/or in contact with the bottom wall 456 of the channel 450. In other embodiments, the tenon 460 of the body of the coupler 430 may have a different geometry complementing the geometry of the channel 450 such that the tenon 460 of the coupler 430 may be slidably disposed in the channel 450 of the elongate member 412. In some embodiments, the configuration of the tenon 460 and the channel 450 may prevent the tenon 460 from being removed from the channel 450 in a direction perpendicular to the longitudinal axis of the elongate member 412.

The tenon 460 of the coupler 430 may be slidably disposed within the channel 450 of the elongate member 412 such that the coupler 430 may be positioned at various locations along the length of the elongate member 412. Additional couplers 430, associated with additional levels of the spinal column, may be slidably disposed in the channel 450 at additional longitudinal locations, as desired. Thus, the channel 450 may receive the tenons 460 of a plurality of couplers 430 therein, such that the couplers 430 can be positioned with a desired spacing between adjacent couplers 430 of the assembly 10. The interaction of the couplers 430 with the channel 450 of the elongate member 412 may provide for a level of adjustability of the assembly 10 when assembled on the spinal column to accommodate various anatomical structures and/or specific dimensions of the spinal column of the patient.

The coupler 430 may include one or more set screws 418, or other fasteners, for securing the coupler 430 at a desired location along the elongate member 412. For example, the coupler 430 may include a threaded bore 419 into which the set screw 418 may be threaded. After sliding the tenon 460 of the coupler 430 to a desired position in the channel 450, the set screw 418 may be tightened, thus securing and/or locking the coupler 430 is a singular fixed position relative to the elongate member 412.

Figure 11:
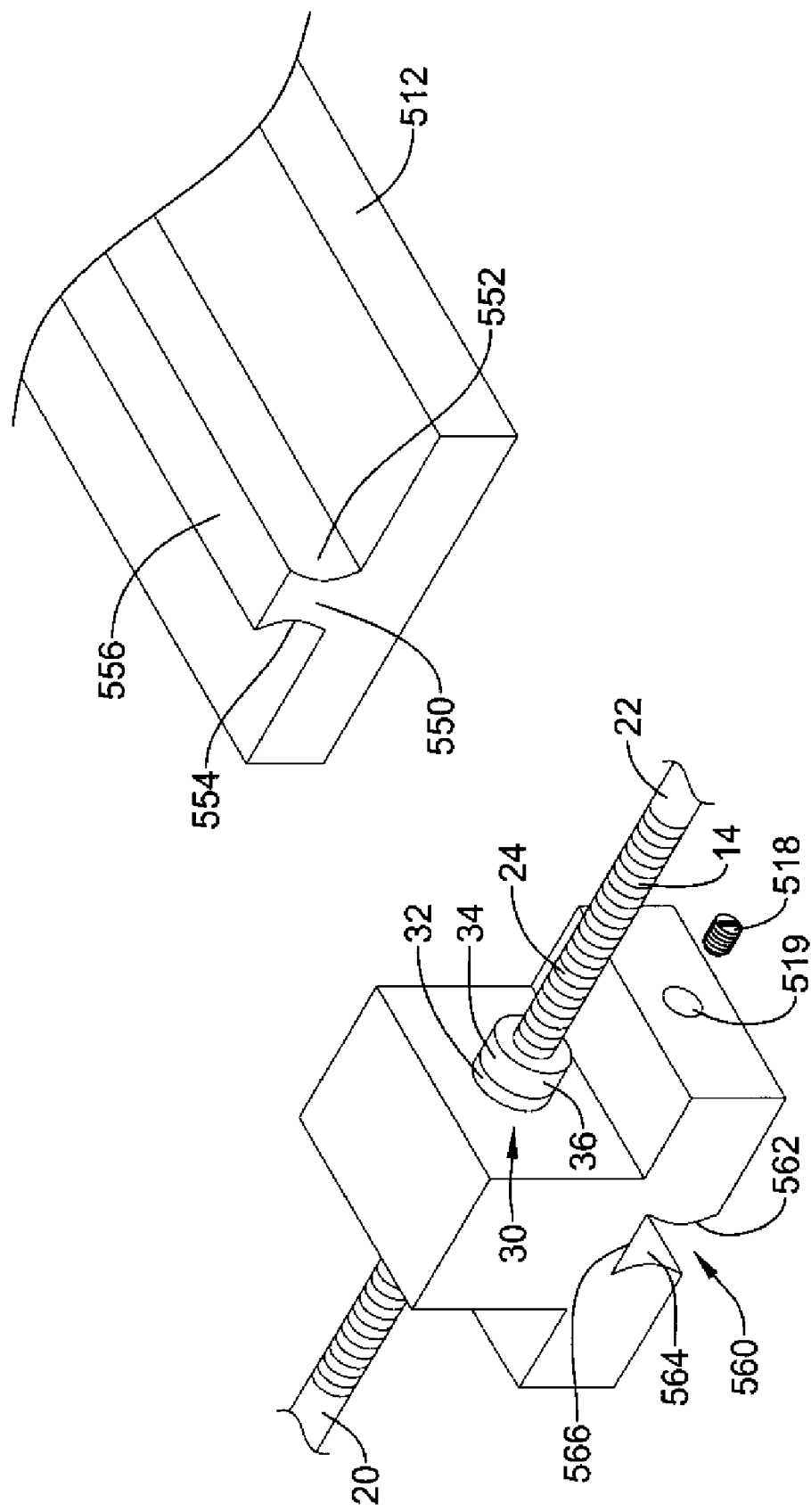
FIG. 11 is a perspective view of yet another exemplary embodiment of an assembly for correcting an abnormal curvature of a spinal segment.

Yet another embodiment of components of the assembly 10 is shown in FIG. 11. As illustrated, the assembly 10 may include an elongate member 512, which may be a variation of the elongate member 12 described above, extending along a posterior portion of the spinal column. The elongate member 512 may include a rail 550 extending along at least a portion of the length of the elongate member 512. In some embodiments, the rail 550 may extend from a superior end of the elongate member 512 to an inferior end of the elongate member 512. In some embodiments, the rail 550 may include first and second side surfaces 552, 554, which may be planar, non-planar, convex and/or concave side surfaces. For example, as shown in FIG. 11, the side surfaces 552, 554 of the rail 550 may be concave, with a central portion closer to one another than end portions of the side surfaces 552, 554. In other embodiments, the side surfaces 552, 554 of the rail 550 may be convex, with end portions closer to one another than the central portion of the side surfaces 552, 554.

The assembly may also include a coupler 530 having a body including a channel 560 shaped, sized and/or configured to mate with the rail 550 of the elongate member 512. For example, the channel 560 of the body of the coupler 530 may be slidably disposed over the rail 550 of the elongate member 412 (i.e., the rail 550 may be positioned in the channel 560) such that the surface 562 of the coupler 530 is facing, parallel to, and/or in contact with the side surface 552 of the rail 550, the surface 564 of the coupler 530 is facing, parallel to, and/or in contact with the side surface 554 of the rail 550, and/or the surface 566 of the coupler 530 is facing, parallel to, and/or in contact with the top surface 556 of the rail 550. For example, the surface 562 of the channel 560 may be a convex surface mating with the concave surface 552 of the rail 550 and/or the surface 564 of the channel 560 may be a convex surface mating with the concave surface 554 of the rail 550. It is noted that if the rail 550 included convex surfaces, then the channel 560 may include concave surfaces configured to mate with the convex surfaces of the rail 550. In other embodiments, the channel 560 of the body of the coupler 530 may have a different geometry complementing the geometry of the rail 550 such that the channel 560 of the coupler 530 may be slidably disposed over the rail 550 of the elongate member 512. In some embodiments, the configuration of the channel 560 and the rail 550 may prevent the rail 550 from being removed from the channel 560 in a direction perpendicular to the longitudinal axis of the elongate member 512.

The channel 560 of the coupler 530 may be slidably disposed over the rail 550 of the elongate member 512 such that the coupler 530 may be positioned at various locations along the length of the elongate member 512. Additional couplers 530, associated with additional levels of the spinal column, may be slidably disposed on the rail 550 at additional longitudinal locations, as desired. Thus, the rail 550 may receive the channels 560 of a plurality of couplers 530 thereon, such that the couplers 530 can be positioned with a desired spacing between adjacent couplers 530 of the assembly 10. The interaction of the couplers 530 with the rail 550 of the elongate member 512 may provide for a level of adjustability of the assembly 10 when assembled on the spinal column to accommodate various anatomical structures and/or specific dimensions of the spinal column of the patient.

The coupler 530 may include one or more set screws 518, or other fasteners, for securing the coupler 530 at a desired location along the elongate member 512. For example, the coupler 530 may include a threaded bore 519 into which the set screw 518 may be threaded. After sliding the coupler 530 along the rail 550 of the elongate member 512 to a desired position, the set screw 518 may be tightened, thus securing and/or locking the coupler 530 is a singular fixed position relative to the elongate member 512.

It is noted that various configurations shown in the drawings and described herein may be adapted for use in the assembly 110 shown in FIGS. 2A and 2B, as well as other assemblies for post-operatively correcting an abnormal curvature of a spinal column.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. An assembly for post-operatively treating an abnormal curvature of vertebrae of a spinal column, the assembly comprising:

an elongate member extending in a generally vertical direction along a posterior side of the spinal column;

a transverse member fastened to a vertebra of the spinal column with a plurality of fasteners and extending in a generally horizontal direction, the transverse member having a threaded region;

a coupler coupling the elongate member to the transverse member, the coupler including a rotating member threadedly engaged with the threaded region of the transverse member; and means for non-invasively rotating the rotating member post-operatively, wherein rotation of the rotating member provides lateral movement of the transverse member relative to the elongate member, thereby moving the vertebra in a horizontal direction.

2. The assembly of claim 1, wherein the threaded region of the transverse member includes a first threaded portion extending from a first side of the elongate member and a second threaded portion extending from a second side of the elongate member opposite the first side.

3. The assembly of claim 2, wherein the threaded region of the transverse member includes threads which continuously extend from the first threaded portion to the second threaded portion.

4. The assembly of claim 1, wherein the elongate member includes an opening, wherein the transverse member extends through the opening of the elongate member.

5. The assembly of claim 4, wherein at least a portion of the coupler extends into the opening of the elongate member, and wherein the transverse member extends through a bore of the coupler.

6. The assembly of claim 5, wherein the threaded region of the transverse member includes a first threaded portion extending from a first side of the coupler and a second threaded portion extending from a second side of the coupler opposite the first side.

7. The assembly of claim 1, wherein the elongate member includes a channel, wherein a portion of the coupler is disposed in the channel.

8. The assembly of claim 1, wherein the elongate member includes a rail, wherein the coupler is disposed over the rail.

9. The assembly of claim 1, wherein the elongate member is connected to a first bone member superior to the vertebra, and wherein the elongate member is connected to a second bone member inferior to the vertebra.

10. The assembly of claim 9, wherein the first bone member is a second vertebra.

11. The assembly of claim 10, wherein the second bone member is a sacrum.

12. The assembly of claim 10, wherein the second bone member is a third vertebra.

13. An assembly for post-operatively treating an abnormal curvature of vertebrae of a spinal column, the assembly comprising:

an elongate member extending in a generally vertical direction along a posterior side of at least three vertebrae of the spinal column;

a first transverse member fixedly attached to a first vertebra of the spinal column with a plurality of fasteners, the first transverse member extending generally perpendicular to the elongate member;

a second transverse member fixedly attached to a second vertebra of the spinal column with a plurality of fasteners, the second transverse member extending generally perpendicular to the elongate member;

a third transverse member fixedly attached to a third vertebra of the spinal column with a plurality of fasteners, the third transverse member extending generally perpendicular to the elongate member;

a first coupler coupling the elongate member to the first transverse member, the first coupler including a fine adjustment mechanism configured to provide non-invasive post-operative movement of the first transverse member in a horizontal direction relative to the elongate member;

a second coupler coupling the elongate member to the second transverse member, the second coupler including a fine adjustment mechanism configured to provide non-invasive post-operative movement of the second transverse member in a horizontal direction relative to the elongate member; and a third coupler coupling the elongate member to the third transverse member, the third coupler including a fine adjustment mechanism configured to provide non-invasive post-operative movement of the third transverse member in a horizontal direction relative to the elongate member.

14. The assembly of claim 13, wherein the fine adjustment mechanism of each of the first, second and third couplers includes a rotating member.

15. The assembly of claim 14, wherein the rotating member of the fine adjustment mechanism of each of the first, second and third couplers includes a threaded portion engaging a threaded portion of the first, second and third transverse members, respectively.

16. The assembly of claim 13, wherein the first transverse member is positioned parallel to the second transverse member and is located a distance away from the second transverse member.

17. The assembly of claim 16, further comprising means for varying the distance between the first transverse member and the second transverse member.

18. The assembly of claim 13, wherein the first transverse member is located a distance away from the second transverse member, and the second transverse member is located a distance away from the third transverse member, wherein the assembly includes means for varying the distances between the transverse members to accommodate anatomical structures of the spinal column.

19. The assembly of claim 13, wherein the elongate member includes a channel, wherein a portion of each of the first, second and third couplers is slidably disposed in the channel.

20. The assembly of claim 13, wherein the elongate member includes a rail, wherein each of the first, second and third couplers is slidably disposed on the rail.

21. The assembly of claim 13, wherein post-operative movement of each of the first, second and third transverse members may be performed independent of post-operative movement of the remainder of the first, second and third transverse members.

22. An assembly for post-operatively treating an abnormal curvature of vertebrae of a spinal column, the assembly comprising:

an elongate member extending in a generally vertical direction along a posterior side of the spinal column and connected to a first bone member, a second bone member superior to the first bone member, and a third bone member superior to the second bone member; and a connector for connecting the elongate member to the second bone member, the connector having a longitudinal axis extending from a first end of the connector to a second end of the connector, the connector including a first end region proximate the first end and a second end region proximate the second end movable relative to the first end region, the first end region secured to the second bone member and including a threaded portion, the second end region connected to the elongate member and including a rotating member have a threaded portion threadedly engaging the threaded portion of the first end region, wherein rotation of the rotating member about the longitudinal axis shortens and/or lengthens the connector along the longitudinal axis such that the distance between the first and second ends of the connector is changed.

23. The assembly of claim 22, wherein rotation of the rotating member draws the second bone member toward the elongate member.

24. A method of treating an abnormal curvature of vertebrae of a spinal column of a patient, the method comprising:
during a surgical operation, performing the following steps i), ii), and iii):
  i) placing an elongate member along a posterior side of the spinal column in a generally vertical direction;
  ii) connecting a transverse member to a first vertebra with a plurality of fasteners, the transverse member including a threaded region;
  iii) coupling the transverse member to the elongate member with a coupler, the coupler including a rotating member having a threaded portion engaging the threaded region of the transverse member; and
post-operatively and non-invasively, performing the following step a):
  a) rotating the rotating member, thereby moving the transverse member in a horizontal direction relative to the elongate member.

25. The method of claim 24, wherein during the surgical operation performing the additional steps of:
  iv) sliding the coupler along the elongate member to a desired position; and
  v) securing the coupler to the elongate member at the desired position.

26. The method of claim 24, wherein during the surgical operation performing the additional steps of:
  iv) connecting a second transverse member to a second vertebra with a plurality of fasteners, the second transverse member spaced from the transverse member by a distance;
  v) adjusting the distance between the transverse member and the second transverse member to a desired distance.

27. The method of claim 26, wherein the adjusting step includes moving the coupler in an opening of the elongate member.

28. The method of claim 26, wherein the adjusting step includes moving a first segment of the elongate member relative to a second segment of the elongate member.

29. The method of claim 26, wherein the adjusting step includes moving the transverse member superiorly and/or inferiorly relative to the plurality of fasteners.

30. The method of claim 26, wherein the adjusting step includes sliding the coupler along the longitudinal axis of the elongate member.

31. The method of claim 26, wherein the desired distance is dependent on vertebral spacing of the spinal column of the patient.

32. The method of claim 24, wherein consequent the step of rotating the rotating member, a corrective force is exerted on the first vertebra.

33. The method of claim 24, wherein the step of rotating the rotating member moves the first vertebra in a horizontal direction relative to a second, adjacent vertebra of the spinal column.

34. An assembly for post-operatively treating an abnormal curvature of a segment of a spinal column including a plurality of vertebrae, the plurality of vertebrae including a superiormost vertebra, an inferiormost vertebra, and one or more medial vertebra between the superiormost vertebra and the inferiormost vertebra, the assembly comprising:
an elongate member extending vertically along a posterior side of the segment of the spinal column between the superiormost vertebra and the inferiormost vertebra;
a plurality of transverse members, each transverse member including a first end, a second end and a length therebetween, each transverse member being secured to one of the plurality of vertebrae;
a plurality of couplers, each coupler including an actuatable member, each of the plurality of couplers being associated with one of the plurality of transverse members;
wherein the elongate member is coupled to each of the plurality of transverse members with one of the plurality of couplers at a coupling location intermediate the first end and the second end of the transverse member; and
means for non-invasively rotating at least one of the actuatable members post-operatively, wherein post-operative actuation of an actuatable member of a coupler moves the associated one of the transverse members in a horizontal direction relative to the elongate member, thereby exerting a corrective force to one of the plurality of vertebrae.

35. The assembly of claim 34, wherein the actuatable member of each coupler includes a rotating member having a threaded portion threadedly engaged with a threaded region of the associated one of the transverse members.

36. The assembly of claim 35, wherein each of the transverse members is independently moveable in a horizontal direction through rotation of the associated rotating member.

37. A method of post-operatively treating an abnormal curvature of a segment of a spinal column of a patient including a plurality of vertebrae, the plurality of vertebrae including a superiormost vertebra, an inferiormost vertebra, and one or more medial vertebra between the superiormost vertebra and the inferiormost vertebra, the method comprising:
providing an elongate member extending vertically along a posterior side of the segment of the spinal column between the superiormost vertebra and the inferiormost vertebra;
providing a plurality of transverse members, each transverse member including a first end, a second end and a length therebetween, each transverse member being secured to one of the plurality of vertebrae;
providing a plurality of couplers, each coupler including an actuatable member, each of the plurality of couplers being associated with one of the plurality of transverse members;
wherein the elongate member is coupled to each of the plurality of transverse members with one of the plurality of couplers at a coupling location intermediate the first end and the second end of the transverse member;
non-invasively actuating a desired one of the actuatable members, thereby moving the associated one of the transverse members in a horizontal direction relative to the elongate member;
wherein moving the transverse member in a horizontal direction applies a corrective force to the vertebra to which the transverse member is attached to in order to gradually correct the abnormal curvature of the segment of the spinal column.

38. The method of claim 37, wherein each of the actuatable members is independently actuatable, allowing each of the transverse members to be independently movable in a horizontal direction through actuation of the associated actuatable member.

* * * * *

UNITED STATES PATENT AND TRADEMARK OFFICE
CERTIFICATE OF CORRECTION

PATENT NO.       : 8,043,338 B2                                    Page 1 of 1
APPLICATION NO.  : 12/327688
DATED            : October 25, 2011
INVENTOR(S)      : Jack A. Dant It is certified that error appears in the above-identified patent and that said Letters Patent is hereby corrected as shown below:

Column 5
Line 38, delete "inferiormnost", and insert therefore -- inferiormost --.

Column 7
Line 47, delete "Arther", and insert therefore -- further --.

Column 9
Line 50, delete "213", and insert therefore -- 2B --.

Signed and Sealed this
Twenty-ninth Day of November, 2011

David J. Kappos
*Director of the United States Patent and Trademark Office*